(12) United States Patent
Zimmer et al.

(10) Patent No.: US 7,407,753 B2
(45) Date of Patent: Aug. 5, 2008

(54) METHODS, KITS AND PHARMACEUTICAL COMPOSITIONS FOR DIAGNOSING, DELAYING ONSET OF, PREVENTING AND/OR TREATING OSTEOPOROSIS

(75) Inventors: Andreas Zimmer, Von-Halberg-Strasse 2, Bonn 53125 (DE); Meliha Karsak, Argelanderstrasse 52, Bonn 53115 (DE); Marie-Christine De Vernejoul, Paris (FR); Itai Bab, Karmei Yossef (IL); Esther Shohami, Mevasseret Zion (IL); Raphael Mechoulam, Jerusalem (IL)

(73) Assignees: Yissum Research Development Company of the HebrewUniversityofJerusalem, Jerusalem (IL); Institut National de la Sante et de la Recherche Medicale, Paris (FR); Andreas Zimmer, Bonn (DE); Meliha Karsak, Bonn (DE)

( * ) Notice: Subject to any disclaimer, the term of this patent is extended or adjusted under 35 U.S.C. 154(b) by 171 days.

(21) Appl. No.: 10/851,667

(22) Filed: May 24, 2004

(65) Prior Publication Data

US 2005/0260608 A1    Nov. 24, 2005

(51) Int. Cl.
C12Q 1/68     (2006.01)
C07H 21/04    (2006.01)
(52) U.S. Cl. .......................... 435/6; 536/23.1
(58) Field of Classification Search ............ None
See application file for complete search history.

(56) References Cited

FOREIGN PATENT DOCUMENTS

| EP | 0451867 | 10/1991 |
|---|---|---|
| WO | WO 92/14481 | 3/1992 |
| WO | WO 92/15712 | 9/1992 |
| WO | WO 2004/103410 | 2/2004 |

OTHER PUBLICATIONS

Munro, Sean et al. Molecular characterization of a peripheral receptor for cannabinoids. 1993. Nature. vol. 365 pp. 61-65.*
Devoto, Marcella et al. Variance component linkage analysis indicates a QTL for femoral neck bone mineral density of chromosome 1p36. 2001 Human Molecular Genetics vol. 10 No. 21 pp. 2447-2452.*
Wacholder, Sholom et al. Assessing the probability that a positive report is false: an approach for molecular epidemiology studies. Journal of the National Cancer Institute. 2004. vol. 96 pp. 434-442.*
Abrams et al. "Comprehensive Detection of Single Base Changes in Human Genomic DNA Using Denaturing Gradient Gel Electrophoresis and A GC Clamp", Genomics, 7: 463-475, 1990.
Abravaya et al. "Molecular Beacons as Diagnostic Tools: Technology and Applications", Clin. Chem. Lab. Med., 41(4): 468-474, 2003.

Iwamura et al. "In Vitro and In Vivo Pharmacological Characterization of JTE-907, A Novel Selective Ligand for Cannabinoid CB2 Receptor", The Journal of Pharmacological and Experimental Therapeutics, 296(2): 420-425, 2001.
Writing Group "Diagnosis of Osteoporosis in Men, Premenopausal Woman, and Children", The Writing Group for the ISCD Position Development Conference, Journal of Clinical Densitometry, 7(1): 17-26, 2004.
Larrick, et al. "PCR Amplification of Antibody Genes", Methods: A Comparison to Methods in Enzymology, 2(2): 106-110, 1991.
Latorra et al. "Enhanced Allele-Specific PCR Discrimination in SNP Genotyping Using 3' Locked Nucleic Acid (LNA) Primers", Human Mutation, 22: 79-85, 2003.
Liljedahl et al. "A Microarray Minisequencing System for Pharmacogenetic Profiling of Antihypertensive Drug Response", Pharmacogenetics, 13: 7-17, 2003.
Day et al. "High-Throughput Genotyping Using Horizontal Polyacrylamid Gels With Wells Arranged for Microplate Array Diagonal Gel Electrophoresis (MADGE)", BioTechniques, 19: 830-835, 1995.
Manolagas et al. "Sex Steroids, Cytokines and the Bone Marrow: New Concepts on the Pathogensis of Osteoporosis", Non-Reproductive Actions of Sex Steroids, Ciba Foundation Symposium 191, p. 187-202, 1995.
Martin "Hormones in the Coupling of Bone Resorption and Formation", Osteoporosis International, Suppl. 1: S121-S125, 1993.
Leushner et al. "Automated Mass Spectrometry: A Revolutionary Technology for Clinical Diagnostics", Molecular Diagnosis, 5(4): 341-348, 2000.
Matsuda et al. "Structure of A Cannabinoid Receptor and Functional Expression of the Cloned cDNA", Nature, 346: 561-564, 1990.
Mauler et al. "BAY 38-7271: A Novel Highly Selective and Highly Potent Cannabinoid Receptor Agonist for the Treatment of Traumatic Brain Injury", CNS Drug Reviews, 9(4): 343-358, 2003.
McKallip et al. "Targeting CB2 Cannabinoid Receptor as A Novel Therapy to Treat Malignant Lymphblastic Disease", Blood, 100(2): 627-634, 2002.
Müller et al. "Micro-Tomographic Imaging for the Nondestructive Evaluation of Trabecular Bone Architecture", Bone Research in Biomechanics, p. 61-79, 1997.
Munro et al. "Molecular Characterization of A Peripheral Receptor for Canabinoids", Nature, 365: 61-65, 1993.
Nickerson et al., "Automated DNA Diagnostics Using An ELISA-Based Oligonucleotide Ligation Assay", Proc. Natl. Acad. Sci. USA, 87: 8923-8927, 1990.
O'Meara et al. "SNP Typing by Apyrase-Mediated Allele-Specific Primer Extension on DNA Microarrays", Nucleic Acids Research, 30(15/e75): 1-8, 2002.
Orita et al. "Rapid and Sensitive Detection of point Mutations and DNA Polymorphisms Using the Polymerase Chain Reaction", Genomics, 5: 874-879, 1989.

(Continued)

Primary Examiner—Sarae Bausch
Assistant Examiner—Amanda Shaw

(57) ABSTRACT

The present invention uncovers a highly significant association of SNPs in the CNR2 locus, encoding the cannabinoid receptor 2 protein, with osteoporosis. Methods and kits for determining predisposition to osteoporosis, improving diagnosis in individuals suspected of having osteoporosis are provided. Also provided a method of identifying a putative osteoporosis-causing genetic mutation in a subject.

1 Claim, 9 Drawing Sheets

OTHER PUBLICATIONS

Pack et al. "Improved Bivalent Miniantibodies, With Identical Avidity as Whole Antibodies, Produced by High Cell Density Fermentation of *Escherichia coli*", Bio/Technology, 11: 1271-1277, 1993.

Parfitt et al. "Bone Histomorphometry: Standartization of Nomenclature, Symbols, and Units", Journal of Bone and Mineral Research, 2(6): 595-610, 1987.

Porter "The Hydrolysis of Rabbit γ-Globulin and Antibodies With Crystalline Papain", The Biochemical Journal, 73: 119-126, 1959.

Rao et al. "Genotyping Single Nucleotide Polymorphisms Directly From Genomic DNA by Invasive Cleavage Reaction on Microspheres", Nucleic Acids Research, 31(11/e66): 1-8, 2003.

Ren et al. "Straightforward Detection of SNPs in Double-Stranded DNA by Using Exonuclease III/Nuclease S1/PNA System", Nucleic Acids Research, 32(4/e42): 1-9, 2004.

Risch et al. "The Future of Genetic Studies of Complex Human Diseases", Science, 273(5281): 1516-1517, 1996.

Ross et al. "Inhibition of Nitric Oxide Production in RAW264.7 Macrophages by Cannabinoids and Plamitoylethanolamide", European Journal of Pharmacology, 401: 121-130, 2000.

Rubin et al. "IGF-I Regulates Osteoprotegerin (OPG) and Receptor Activator of Nuclear Factor-κB Ligand In Vitro and OPG In Vivo", The Journal of Clinical Endocrinology & Metabolism, 87(9): 4273-4279, 2002.

Sauer et al. "Extension of the GOOD Assay for Genotyping Single Nucleotide Polymorphisms by Matrix-Assisted Laser Desorption/Ionization Mass Spectrometry", Rapid Communications in Mass Spectrometry, 17: 1265-1272, 2003.

Scholz et al. "Rapid Screening for Tp53 Mutations by Temperature Gradient Gel Electrophoresis: A Comparison With SSCP Analysis", Human Molecular Genetics, 2(12): 2155-2158, 1993.

Sheffield et al. "Attachment of A 40-Base-Pair G+C-Rich Sequence (CG-Clamp) to Genomic DNA Fragments by the Polymerase Chein Reaction Results in Improved Detection of Single-Base Changes", Proc. Natl. acad. Sci. USA, 86: 232-236, 1989.

Shi "Enabling Large-Scale Pharmacogenetic Studies by High-Throughput Mutation Detection and Genotyping Technologies", Clinical Chemistry, 47(2): 164-172, 2001.

Shire et al. "An Amino-Terminal Variant of the Central Cannabinoid Receptor Resulting From Alternative Splicing", The Journal of Biological Chemistry, 270(8): 3726-3731, 1995.

Slatkin et al. "Testing for Linkage Disequilibrium in Genotypic Data Using the Expectation-Maximization Algorithm", Heredity, 76: 377-383, 1995.

Smith et al. "Novel Method of Detecting Single Base Substitutions in RNA Molecules by Differential Melting Behavior in Solution", Genomics, 3: 217-223, 1988.

Solinas et al. "Duplex Scorpion Primers in SNP Analysis and FRET Applications", Nucleic Acids Research, 29(20/e96): 1-9, 2001.

Tõnisson et al. "Unravelling Genetic Data by Arrayed Primer Extension", Clin. Chem. Lab. Med., 38(2): 165-170, 2000.

Turner et al. "Typing of Multiple Single Nucleotide Polymorphisms in Cytokine and Receptor Genes Using SNaPshot", Human Immunology, 63: 508-513, 2002.

Wartell et al. "Detecting Base Pair Substitutions in DNA Fragments by Temperature-Gradient Gel Electrophoresis", Nucleic Acids Research, 18(9): 2699-2705, 1990.

Whitlow et al. "Single-Chain Fv Proteins and Their Fusion Proteins", Methods: A Companion to Methods in Enzymology, 2(2): 97-105, 1991.

Liu et al. "Molecular Studies of Identification of Genes for Osteoporosis: The 2002 Update", Journal of Endocrinology, 177: 147-196, 2003.

Zou et al. "CpG Oligonucleotides: Novel Regulators of Osteoclast Differentiation", The FASEB Journal, 16: 274-282, 2002.

Bird et al. "Single-Chain Antigen-Binding Proteins", Science, 242(4877): 423-426, 1988.

Lerman et al. "Computational Simulation of DNA Melting and Its Application to Denaturing Gradient Gel Electrophoresis", Methods in Enzymology, 155(30): 482-501, 1987.

Akula et al. "Utility and Accuracy of Template-Directed Dye-Terminator Incorporation With Fluorescence-Polarization Detection for Genotyping Single Nucleotide Polymorphism", BioTechniques, 32(5): 1072-1078, 2002.

Ammann et al. "Bone Strength and Its Determinants", Osteoporosis International, 14(Suppl.3): S13-S18, 2003.

Bab et al. "Histone H4-Related Osteogenic Growth Peptide (OGP): A Novel Circulating Stimulator of Osteoblastic Activity", The EMBO Journal, 11(5): 1867-1873, 1992.

Beaudet et al. "Homogeneous Assays for Single-Nucleotide Polymorphism Typing Using AlphaScreen", Genome Research, 11: 600-608, 2001.

Bell et al. "SNPstream UHT: Ultra-High Throughput SNP Genotyping for Pharmacogenomics and Drug Discovery", BioTechniques, 32: S70-S77, 2002.

Børresen et al. "Constant Denaturant Gel Electrophoresis as A Rapid Screening Technique for P53 Mutations", Proc. Natl. Acad. Sci. USA, 88: 8405-8409, 1991.

Buckley et al. "Immunomodulaton by Cannabinoids Is Absent in Mice Deficient for the Cannabinoid CB2 Receptor", European Journal of Pharmacology, 396: 141-149, 2000.

Burgener et al. "Fluoride Increases Tyrosine Kinase Activity in Osteoblast-Like Cells: Regulatory Role for the Stimulation of Cell Proliferation and Pi Transport Across the Plasma Membrane", Journal of Bone and Mineral Research, 10(1): 164-171, 1995.

Cashman et al. "Population Distribution of Human Flavin-Containing Monooxygenase Form 3: Gene Polymorphism", Drug Metabolism and Disposition, 29(12): 1629-1637, 2001.

Chang et al. "Effects of Cannabinoids on LPS-Stimulated Inflammatory Mediator Release Macrophages: Involvement of Eicosanois", Journal of Cellular Biochemistry, 81: 715-723, 2001.

Conner et al. "Deetection of Sickle Cell βS-Globin Allele by Hybridization With Synthetic Oligonucleotides", Proc. Natl. Acad. Sci. USA, 80: 278-282, 1983.

Cordell et al. "A Unified Stepwise Regression Procedure for Evaluating the Relative Effects of Polymorphisms Within A Gene Using Case/Control of Family Data: Application to HLA in Type 1 Diabetes", American Journal of Human Genetics, 70: 124-141, 2002.

Curcio et al. "Multiplex High-Throughput Solid-Phase Minisequencing by Capillary Electrophoresis and Liquid Core Waveguide Fluorescence Detection", Electrophoresis, 23: 1467-1472, 2002.

Howell et al. "Dynamic Allele-Specific Hybridization", Nature Biotechnology, 17: 87-88, 1999.

Devane et al. "Determination and Characterization of A Cannabinoid Receptor in Rat Brain", Molecular Pharmacology, 34: 605-613, 1988.

Devlin et al. "A Comparison of Linkage Disequilibrium Measures for Fine-Scale Mapping", Genomics, 29: 311-322, 1995.

Erlebacher et al. "Increased Expression of TGF-β2 in Osteoblasts Results in An Osteoporosis-Like Phenotype", The Journal of Cell Biology, 132(1 & 2): 195-210, 1996.

Fan et al. "Parallel Genotyoing of Human SNPs Using Generic High-Density Oligonucleotide Tag Arrays", Genome Research, 10: 853-860, 2000.

Fontanges et al. "Osteoporosis and Breast Cancer", Joint Bone Spine, 71: 102-110, 2004.

Frenkel et al. "Activity of the Osteocalcin Promoter in Skeletal Sites of Transgenic Mice and During Osteoblast Differentiation in Bone Marrow-Derived Stromal Cell Cultures: Effects of Age and Sex", Endocrinology, 138(5): 2109-2116, 1997.

Gasparini et al. "Analysis of 31 CFTR Mutations by Polymerase Chain Reaction/Oligonucleotide Ligation Assay in A Pilot Screening of 4476 Newborns for Cystic Fibrosis", J. Med. Screen., 6: 67-69, 1999.

Germer et al. "Single-Tube Genotyping Without Oligonucleotide Probes", Genome Research, 9: 72-78, 1999.

Gogos et al. "Detection of Single Base Mismatches of Thymine and Cytosine Residues by Potassium Permanganate and Hydroxylamine in the Presence of Tetralkylammonium Salts", Nucleic Acids Research, 18(23): 6807-6814, 1990.

Howlett et al. "International Union of Pharmacology. XXVII. Classification of Cannabinoid Receptors", Pharmacological Reviews, 54(2): 161-202, 2002.

Hanuš et al. "HU-308: A Specific Agonist for CB2, A Peripheral Cannabinoid Receptor", Proc. Natl. Acad. Sci. USA, 96(25): 14228-14233, 1999.

Hanuš et al. "2-Arachidonyl Glyceryl Ether, An Endogenous Agonist of the Cannabinoid CB1 Receptor", Proc. Natl. Acad. Sci. USA, 98(7): 3662-3665, 2001.

Hildebrand et al. "Direct Three-Dimensional Morphometric Analysis of Human Cancellous Bone: Microstructural Data From Spine, Femur, Iliac Crest, and Calcaneus", Journal of Bone and Mineral Research, 14(7): 1167-1174, 1999.

Holland et al. "Detection of Specific Polymerase Chain Reaction Product by Utilizing the 5'->3' Exonuclease Activity of Thermus Aquaticus DNA Polymerase", Proc. Natl. Acad. Sci. USA, 88: 7276-7280, 1991.

Hsu et al. "Universal SNP Genotyping Assay With Fluorescence Polarization Detection", BioTechniques, 31(3): 560-570, 2001.

Inbar et al. "Localization of Antibody-Combining Sites Within the Variable Portions of Heavy and Light Chains", Proc. Natl. Acad. Sci. USA, 69(9): 2659-2662, 1972.

Ishac et al. "Inhibition of Exocytotic Noradrenaline Release by Presynaptic Cannabinoid CB1 Receptors on Peripheral Sympathetic Nerves", British Journal of Pharmacology, 118: 2023-2028, 1996.

* cited by examiner

METHODS, KITS AND PHARMACEUTICAL COMPOSITIONS FOR DIAGNOSING, DELAYING ONSET OF, PREVENTING AND/OR TREATING OSTEOPOROSIS

FIELD AND BACKGROUND OF THE INVENTION

The present invention relates to methods, kits and pharmaceuticals compositions useful for diagnosing, delaying onset of, preventing and/or treating osteoporosis and, more particularly, to the identification of an osteoporosis risk haplotype using SNPs present in the CNR2 locus.

Osteoporosis is a systemic skeletal disease resulting in low bone mass and micro-architectural deterioration of bone tissue, causing an increase in bone fragility and susceptibility to fracture. If not prevented or if left untreated, osteoporosis can painlessly result in multiple bone fractures.

Bone tissue, which is mainly composed of collagen and calcium phosphate, is subjected to a constant breakdown and resynthesis (i.e., bone remodeling) in a process mediated by osteoblasts, which produce new bone, and osteoclasts, which destroy the bone. The activities of these cells are regulated by a large number of cytokines and growth factors, many of which have now been identified and cloned.

During childhood and teenage years, the total amount of new bone added is higher than the amount of bone removed and resorbed resulting in a net increase in bone mass. However, beyond the age of about twenty-five to thirty-five, bone resorption slowly begins to exceed bone formation, leading to a net bone loss. Thus, the appearance of osteoporosis and bone fractures is dependent on the peak bone mass accumulated until the age of 25-35 years and the rate of bone mass loss following that peak.

Due to estrogen deficiency following menopause, bone loss is more pronounced in females than in males. In the USA, osteoporosis affects 17% of all postmenopausal women and 30% of women older than 65.

The diagnosis of osteoporosis relies on the measurements of bone density, which is calculated and presented as T-scores. However, the predictability of bone density measurement is relatively low. In addition, more than 75% of women and about 90% of men with a high likelihood of developing osteoporosis are not being tested. Furthermore, in children and adolescents, in whom physical exercise can still affect and increase the peak of bone mass, no densitometric criteria are available (J. Clin. Densitom. 2004, 7: 17-26. The Writing Group for the ISCD Position Development Conference).

Thus, there is a need to develop accurate methods of determining susceptibility towards osteoporosis in both human mates and females at any age.

Osteoporosis-related bone fractures are treated using casts, braces, anchoring devices and other strictly mechanical means. The fractured bone is often replaced by endosseous implants. On the other hand, treatment of the skeletal deterioration associated with post-menopausal osteoporosis is based on the use of bisphosphonates and estrogens, both of which prevent bone loss. However, the use of bisphosphonates may result in serious side effects in the upper gastrointestinal track. Moreover, after several years of treatment, bisphosphonates restrain bone remodeling. This may, in-turn, lead to increased fracture risk. In addition, the use of estrogens may result in increased risks for breast cancer, stroke and cardiovascular diseases (Fontanges E., et al., 2004. Osteoporosis and breast cancer. Joint Bone Spine. 71: 102-10).

Other treatment regimens for osteoporosis include the administration of Teriparatide, a form of the parathyroid hormone, which stimulates new bone formation and significantly increases bone mineral density. However, the use of Teriparatide is often associated with nausea, leg cramps and dizziness. Moreover, the major disadvantage of the use of a parathyroid hormone for preventing osteoporosis is the need of daily injections.

Various other therapeutic approaches of treating bone-related diseases have been suggested. These include the use of osteogenic growth polypeptides for the enhancement of bone formation (U.S. Pat. No. 5,461,034), antiestrogenic oral contraceptive compounds, 3,4-diarylchromans, for the treatment of osteoporosis (U.S. Pat. No. 5,280,040), a recombinant protein containing a bone morphogenic polypeptide (BMP) of the TGF-beta (TGF-β) superfamily of cytokines for enhancing bone growth (U.S. Pat. No. 6,352,973), inhibitors of proteasomal activity and production for inhibiting osteoclastic activity and stimulating bone growth (U.S. Pat. No. 6,462,019), activin and bone morphogenic protein (International patent application No. 92/14481), cell growth factor which induces osteoblast proliferation (European Patent Application No. 499 242), antagonists of parathyroid hormone peptide for the treatment of dysbolism associated with calcium or phosphoric acid, such as osteoporosis (European Patent Application No. 451 867), and fluorides, which increase osteoblast proliferation (Burgener et al. J Bone Min Res (1995) 10:164-171).

Although bone morphogenic proteins (BMPs) are potent stimulators of bone formation in vitro and in vivo, their use as therapeutic agents in enhancing bone healing is limited by the wide-expression of BMP receptors in a large variety of tissues, making BMP's systemic administration essentially unpractical.

On the other hand, the administration of fluorides is often associated with increased bone fragility, presumably due to adverse effects on bone mineralization.

Thus, there is currently a need for developing a safe and useful method and/or composition for preventing and/or treating osteoporosis.

Osteoporosis is a multi-factorial disease, depending on both environmental and genetic factors. Twin studies have shown that genetic factors account for 60-80% of the variance in bone mineral density (BMD).

In order to identify the gene(s) underlying the genetic basis of osteoporosis, numerous linkage analysis studies, case-control association studies and quantitative trait locus (QTL) mapping in animal models were conducted (Reviewed in Yao-Zhong, L., et al., 2003, J. of Endocrinology, 177: 147-196). While linkage analysis studies have implicated a mutation in the interleukin-6 (IL6) gene, several association studies suggested that polymorphisms in the Collagen type 1 α1 (COL1A1) gene and possibly also in the vitamin D receptor (VDR) and calcitonin receptor (CTR) genes, are associated with osteoporosis. However, other association studies suggested a relationship between susceptibility to osteoporosis and genetic variations in the 5'-flanking region of the RIL gene encoding a PDZ-LIM domain protein (Omasu et al. 2003, Association of genetic variation of the RIL gene, encoding a PDZ-LIM domain protein and localized in 5q31.1, with low bone mineral density in adult Japanese women. J. Hum. Genet. 48: 342-345) or with exon 10 of the low-density-lipoprotein-receptor-related receptor-related protein 5 (LRP5) gene (Mizuguchi et al. 2004. LRP5, low-density-lipoprotein-receptor-related protein 5, is a determinant for bone mineral density. J. Hum. Genet. 49: 80-86).

While reducing the present invention to practice, the present inventors have uncovered that mice lacking the CB2 receptor gene (CNR2) exhibit low bone mass and high bone turnover. In addition, the present inventors have uncovered that SNPs in the CNR2 locus are highly associated with osteoporosis and that such SNPs can be used in determining predisposition to osteoporosis.

SUMMARY OF THE INVENTION

According to one aspect of the present invention there is provided a method of determining if an individual is predisposed to osteoporosis, the method comprising determining a presence or absence, in a homozygous or heterozygous form, of at least one osteoporosis-associated genotype in the CNR2 locus or in neighboring loci of the individual, the neighboring loci being in linkage disequilibrium with the CNR2 locus, thereby determining if the individual is predisposed to osteoporosis.

According to another aspect of the present invention there is provided a method of improving diagnosis of osteoporosis in an individual, the method comprising determining a presence or absence in a homozygous or heterozygous form, of at least one osteoporosis-associated genotype in the CNR2 locus or in neighboring loci of the individual suspected of having osteoporosis, the neighboring loci are in linkage disequilibrium with the CNR2 locus, thereby improving diagnosis of osteoporosis in the individual.

According to yet another aspect of the present invention there is provided a kit for determining if an individual is predisposed to osteoporosis, the kit comprising at least one reagent for determining a presence or absence in a homozygous or heterozygous form, of at least one osteoporosis-associated genotype in the CNR2 locus or in neighboring loci of the individual, the neighboring loci are in linkage disequilibrium with the CNR2 locus.

According to still another aspect of the present invention there is provided a method of determining if an individual is predisposed to osteoporosis comprising obtaining a DNA sample from the individual, identifying presence or absence of an haplotype consisting of a cytosine nucleotide—containing allele of SNP hCV79667 set forth in SEQ ID NO:11, an adenosine nucleotide—containing allele of SNP hCV11546265 set forth in SEQ ID NO:12, and a guanine nucleotide—containing allele of SNP hCV515481 set forth in SEQ ID NO:14 in the DNA sample, wherein presence indicates increased predisposition risk to osteoporosis.

According to an additional aspect of the present invention there is provided a method of identifying a putative osteoporosis-causing genetic mutation in a subject, comprising identifying at least one nucleic acid substitution in a coding or regulatory nucleic acid sequence being: (a) within a chromosomal sequence region encompassed by SNP hCV79667 and SNP rs2501432, or (b) being in linkage to the chromosomal sequence region, thereby identifying the putative osteoporosis-causing genetic mutation in the subject.

According to still an additional aspect of the present invention there is provided an antibody or antibody fragment capable of specifically binding at least one polymorph of a CB2 protein, the at least one polymorph being an Arginine or an Glutamine residue at position 63 of the CB2 protein set forth in SEQ ID NO:26 (NP_001832), the antibody being capable of differentiating between the Arginine or the Glutamine via differential antibody interaction.

According to further features in preferred embodiments of the invention described below, the at least one osteoporosis-associated genotype in the CNR2 locus is a cytosine nucleotide—containing allele of SNP hCV79667 set forth in SEQ ID NO:11.

According to still further features in the described preferred embodiments the at least one osteoporosis-associated genotype in the CNR2 locus is an adenosine nucleotide—containing allele of SNP hCV11546265 set forth in SEQ ID NO:12.

According to still further features in the described preferred embodiments the at least one osteoporosis-associated genotype in the CNR2 locus is a guanine nucleotide—containing allele of SNP hCV515481 set forth in SEQ ID NO:14.

According to still further features in the described preferred embodiments the at least one osteoporosis-associated genotype in the CNR2 locus is an allelic haplotype comprising at least two of: a cytosine nucleotide—containing allele of SNP hCV79667 set forth in SEQ ID NO:11; an adenosine nucleotide—containing allele of SNP hCV11546265 set forth in SEQ ID NO:12; and a guanine nucleotide—containing allele of SNP hCV515481 set forth in SEQ ID NO:14.

According to still further features in the described preferred embodiments the at least one osteoporosis associated genotype in the CNR2 locus is a guanine nucleotide—containing allele of SNP rs2502992 and/or a cytosine nucleotide—containing allele of SNP rs2501432.

According to still further features in the described preferred embodiments the kit further comprising packaging material packaging at least one reagent and a notification in or on the packaging material, the notification identifying the kit for use in determining if an individual is predisposed to osteoporosis.

According to still further features in the described preferred embodiments the notification also provides for instructions of using the kit in determining if an individual is predisposed to osteoporosis.

According to still further features in the described preferred embodiments the at least one reagent is an oligonucleotide sequence capable of specifically hybridizing with at least one allele of an SNP selected from the group consisting of SNP hCV79667, SNP hCV11546265, and SNP hCV515481.

According to still further features in the described preferred embodiments the at least one reagent is designed so as to be utilizable in a method selected from the group consisting of restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis, Dideoxy fingerprinting (ddF), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, MassEXTEND, MassArray, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Rolling circle amplification, and Invader assay.

According to still further features in the described preferred embodiments the at least one reagent includes Assays-On-Demand™ ID numbers C 79667, C 11546265, and C 515481.

According to still further features in the described preferred embodiments the at least one reagent is an antibody capable of differentially binding at least one polymorph of a CB2 protein, the at least one polymorph being an Arginine or an Glutamine residue at position 63 of the CB2 protein set forth in SEQ ID NO:26 (NP_001832), the antibody being capable of differentiating between the Arginine or the Glutamine via differential antibody interaction.

According to still further features in the described preferred embodiments the CB2 protein—containing biological sample is selected from the group consisting of: blood, bone marrow, skill, muscle, cartilage, lymph nodes, myometrium, placenta, buccal cells.

According to still further features in the described preferred embodiments at least one nucleic acid change is selected from the group consisting of: a missense mutation, a nonsense mutation, a frameshift mutation, a readthrough mutation, a promoter mutation, a regulatory mutation, a deletion, an insertion, an inversion, and a duplication.

The present invention successfully addresses the shortcomings of the presently known configurations by providing methods and kits for determining predisposition and improving diagnosing of osteoporosis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-b—RT-PCR analyses of MC3T3 E1 preosteoblastic (FIG. 1a) and stromal (FIG. 1b) cells derived from murine bone marrow and undergoing osteoblastic differentiation in the presence of osteogenic medium. PTHRcl=PTH receptor 1; TNSALP=tissue nonspecific alkaline phosphatase; NOM=cells grown for 20 days in non-osteogenic medium; PC=RT-PCR positive controls, for CB1 RT—PCR—RNA from cerebellum, for CB2 RT-PCR—RNA from macrophages. Negative results were determined following 45 PCR cycles; FIG. 1c—an RT-PCR analysis of a primary osteoclastogenic murine bone marrow derived monocyte culture. Mono=monocyte stage, Ocl—osteoclast stage; FIGS. 1d-e—immunohistochemical analyses of CB2 receptors in distal femoral metaphysis of wild-type (FIG. 1d) and $CB2^{-/-}$ (FIG. 1e) mice. Immunohistochemical staining was carried out using a rabbit anti-human polyclonal antibody (Cayman Chemical, Ann Arbor, Mich., Cat. No. 101550). Note the presence of CB2-positive osteoblasts (arrowheads), osteocytes (double arrowhead) and osteoclasts (arrows) in wild-type mice (FIG. 1d) but not in $CB2^{-/-}$ mice (FIG. 1e). T—trabecule bone; FIG. 1f—the number of preosteoblasts differentiated from bone marrow-derived stromal cells challenged with the CB2 agonist HU-308. Positive control cultures were challenged with osteogenic growth peptide, an established osteoblastic mitogen [Bab, I., et al. 1992, Histone H4-related osteogenic growth peptide (OGP): a novel circulating stimulator of osteoblastic activity. EMBO J. 11: 1867-1873]; Negative control cultures were challenged with the CB1 aganist Noladin ether [Hanus, L., et al., (2001). 2-arachidonyl glyceryl ether, an endogenous agonist of the cannabinoid CB1 receptor. Proc. Natl. Acad. Sci. U.S.A. 98: 3662-3665]. FIG. 1g—the effect of HU-308 on the number of TRAP-positive multinucleated osteoclasts formed in primary osteoclastogenic monocyte culture.

FIG. 2a-f—μCT analyses of the distal femoral metaphysis depicting trabecular bone volume density in females (FIG. 2a), and males (FIG. 2b), trabecular number in females (FIG. 2c) and males (FIG. 2d), and trabecular thickness in females (FIG. 2e) and males (FIG. 2f); FIGS. 2g-i—histomorphometric analyses of the distal femoral metaphysis in females depicting trabecular osteoclast number (FIG. 2g), trabecular mineral appositional rate (FIG. 2h) and bone formation rate (FIG. 2i); FIGS. 2j-k—μCT analyses of the femoral mid-diaphysis in females (FIG. 2j) and males (FIG. 2k) depicting the average overall diaphyseal diameter (Diaph. Dia) and the diameter of the medullary cavity (Medul. Dia); *=p<0.05.

FIGS. 4a-c—μCT analysis of the distal femoral metaphysis depicting trabecular bone volume density (FIG. 4a), trabecular number (FIG. 4b) and trabecular thickness (FIG. 4c); FIGS. 4d-e—histomorphometric analyses of the distal femoral metaphysis depicting osteoclast number (FIG. 4d) and bone formation rate (FIG. 4e); FIGS. 4f-g—μCT and histomorphometric analyses of the femoral mid-diaphysis depicting cortical thickness and medullary cavity volume density (FIG. 4f) and endocortical mineral appositional rate (FIG. 4g); *, p<0.05

DESCRIPTION OF THE PREFERRED EMBODIMENTS

Figure 1A:
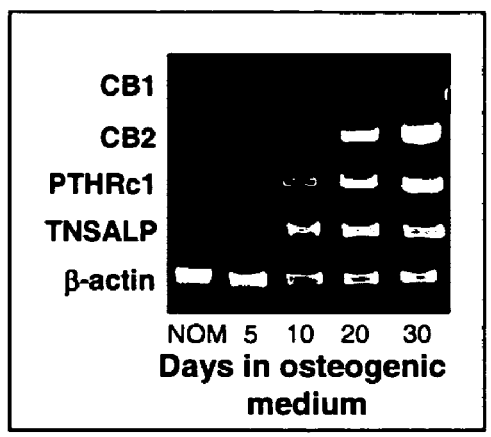
FIGS. 1a-g illustrate CB2 expression and activity in the bone.

The present invention is of methods and kits which can be used to determine predisposition to osteoporosis.

The principles and operation of the methods and kits for determining predisposition to osteoporosis according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Osteoporosis is a systemic skeletal disease which leads to low bone mass and micro-architectural deterioration of bone tissue, and as a result to an increase in bone fragility and susceptibility to bone fractures. The appearance of osteoporosis and bone fractures is dependent on the peak of bone mass accumulated until the age of 25-35 years and the rate of bone mass loss following that peak. Thus, osteoporosis is more prevalent among elderly individuals, especially in women in whom the rate or bone loss is increased following menopause.

Current methods of diagnosing and predicting the risk of osteoporosis rely on measurements of bone density. However, the predictability power of bone density measurements is relatively low. Moreover, in children and adolescents, in whom specific physical exercising can increase the peak of bone mass, no densitometric criteria are available.

While reducing the present invention to practice, the present inventors have uncovered that SNPs in the CNR2 locus and protein polymorphs encoded thereby are highly associative with osteoporosis and thus can be used in determining predisposition to osteoporosis in an individual.

Thus, according to one aspect of the present invention there is provided a method of determining if an individual is predisposed to osteoporosis.

As used herein, the term "individual" includes both young and old human beings of both sexes. Preferably, this term encompasses individuals who are at risk to develop osteoporosis, for example, pre- and post-menopause women, young children and adolescence who have first-degree relatives with osteoporosis, individuals which are suspected of having osteoporosis due to the present of bone fractures and the like.

As used herein, the term "predisposed" when used with respect to osteoporosis refers to an individual which is more susceptible to developing osteoporosis than non-predisposed individuals. Thus, a predisposed individual is more likely to develop osteoporosis than a non-predisposed individual.

The method according to this aspect of the present invention is effected by determining a presence or absence, in a homozygous or heterozygous form, of at least one osteoporosis-associated genotype in the CNR2 locus or in neighboring loci of the individual which are in linkage disequilibrium with the CNR2 locus.

As used herein the term "CNR2 locus" refers to a specific DNA sequence region in the human genome encompassing a gene coding for the cannabinoid receptor 2 (CB2) protein and located on the short arm of chromosome 1 (1p36).

The terms "homozygous" or "heterozygous" refer to two identical or two different alleles, respectively, of a certain polymorphism.

The term "polymorphism" refer, to the occurrence of two or more genetically determined variant forms (alleles) of a particular nucleic acid at a frequency where the rarer (or rarest) form could not be maintained by recurrent mutation alone. A single nucleotide polymorphism (SNP) results from a single base difference between related alleles at the same genetic locus. A non-limiting example of a polymorphism is the presence of a cytosine or guanine nucleotide in SNP hCV79667 (rs4649119).

As is shown in Example 3 of the Examples section which follows, the present inventors have uncovered several SNPs which are highly associative with osteoporosis.

As is shown in Table 6 in the Examples section which follows, the present inventors uncovered that the C allele of SNP hCV79667 (rs4649119) set forth in SEQ ID NO:11 is more prevalent in osteoporosis cases than in control individuals (63% in cases vs. 57% in controls). Moreover, as is further shown in Table 7 in the Examples section which follows, the association of the C allele and CC genotype of SNP hCV79667 with osteoporosis is highly significant (allele: $p=3\times10^{-5}$, OR 1.9; 95% C.I. 1.41-2.57; genotype: $p=4\times10^{-5}$, OR 4.01; 95% C.I. 2.1-7.68).

The present inventors have also uncovered that while the A allele of SNP hCV11546265 set forth in SEQ ID NO:12 is moderately associated with osteoporosis ($p=5.7\times10^{-2}$), the G allele and the GG genotype of SNP hCV515481 (rs4649124) set forth in SEQ ID NO:14 are highly associated with osteoporosis (allele: $p=1.2\times10^{-3}$; genotype: $p=5.7\times10^{-4}$, see Example 3 of the Examples section which follows).

Thus, according to preferred embodiments of the present invention the osteoporosis-associated genotype identified by the present method is the C allele of SNP hCV79667, the A allele of SNP hCV11546265, and/or the G allele of SNP hCV515481.

Moreover, it was unexpectedly found that the C-A-G haplotype of SNPs hCV79667-hCV11546265-hCV515481 is highly and most significantly associated with osteoporosis (P value=$1.87\times10^{-27}$). This is a highly significant association for a complex genetic disease, demonstrating an extremely high likelihood that the osteoporosis-causing mutation(s) resides within the CNR2 locus.

Thus, according to preferred embodiments of the present invention, the allelic haplotype identified by the method of the present invention is characterized by at least two SNPs of the SNPs listed above. Preferably, the allelic haplotype is characterized by the C allele of SNP hCV79667 and the G allele of SNP hCV515481. Most preferably, the allelic haplotype identified by the method of the present invention includes all three CNR2 genotypes, namely, the cytosine nucleotide—containing allele of SNP hCV79667 set forth in SEQ ID NO:11, the adenosine nucleotide—containing allele of SNP hCV11546265 set forth in SEQ ID NO:12 and the guanine nucleotide—containing allele of SNP hCV515481 set forth in SEQ ID NO:14.

The present inventors have also uncovered that the G allele of the non-synonymous SNP rs2502992 and the C allele (a G in the CB2 mRNA) of the non-synonymous SNP rs2501432 are in tight linkage disequilibrium with the G allele of SNP hCV515481 (see Example 3 of the Examples section) and therefore can be also associated with osteoporosis. Interestingly, the rare alleles of both of these non-synonymous SNPs form a CAA→CGG missense mutation in the CNR2 mRNA (GenBank Accession No. NM_001841) resulting in a Gln63Arg amino acid substitution in the CB2 protein (GenBank Accession, No. NP_001832).

Thus, according to preferred embodiments of the present invention the osteoporosis-associated genotype identified by the present method is the G allele of SNP rs2502992 and/or the C allele of SNP rs2501432.

The phrase "neighboring loci" is used herein to describe DNA sequences (either genes or intergenic sequences) that arc in close vicinity of the CNR2 locus and that include other SNPs that are in linkage disequilibrium with SNPs in the CNR2 locus.

The phrase "linkage disequilibrium" (LD) is used to describe the statistical correlation between two neighboring polymorphic genotypes. Typically, LD refers to the correlation between the alleles of a random gamete at the two loci, assuming Hardy-Weinberg equilibrium (statistical independence) between gametes. LD is quantified with either Lewontin's parameter of association (D') or with Pearson correlation coefficient (r) [Devlin B, Risch N. (1995). A comparison of linkage disequilibrium measures for fine-scale mapping. Genomics. 29: 311-322.]. Two loci with a LD value of 1 are said to be in complete LD. At the other extreme, two loci with a LD value of 0 are termed to be in linkage equilibrium. Linkage disequilibrium is calculated following the application of the expectation maximization algorithm (EM) for the estimation of haplotype frequencies [Slatkin M, Excoffier L. (1996). Testing for linkage disequilibrium in genotypic data using the Expectation-Maximization algorithm. Heredity. 76: 377-83.]. Preferably, LD values according to the present invention for neighboring genotypes/loci are selected above 0.1, preferably, above 0.2, more preferable above 0.5, more preferably, above 0.6, still more preferably, above 0.7, preferably, above 0.8, more preferably above 0-9, ideally about 1.0 to 1.0.

Thus, it was surprisingly found by the present inventors that SNPs hCV515477, hCV515482, rs2502992 and rs2501432 are in complete linkage disequilibrium (LD) with SNP hCV515481. Taking into consideration that the likelihood of recombination effects between SNPs which are in complete linkage disequilibrium is negligible, the status of genotypes (i.e., the presence or absence) of SNP hCV515481 can reflect the status of genotypes of any of the hCV515477, hCV515482, rs2502992, rs2501432 SNPs which are in tight LD.

Thus, according to preferred embodiments of the present invention, SNPs which are in linkage disequilibrium with at least one of the SNPs selected from the group consisting of SNP hCV79667, SNP hCV11546265, SNP hCV515481 can also be used in determining predisposition of osteoporosis.

The predisposition to osteoporosis can be quantified by generating and using genotype relative risk (GRR) values. The GRR is the increased chance of an individual with a particular genotype to develop the disease. Thus, the GRR of the risk genotype G, with respect to the protective genotype $G_0$, is the ratio between the risk of an individual carrying genotype G to develop the disease, and the risk of an individual carrying genotype $G_0$ to develop the disease. The GRR used herein is represented in terms of an appropriate odds ratio (OR) of G versus $G_0$ in cases and controls. Moreover, computation of GRR of haplotypes is based on a multiplicative model in which the GRR of an homozygote individual is the square of the GRR of an heterozygote individual. For further details see Risch and Merikangas, 1996 [The future of genetic studies of complex human diseases. Science 273: 1516-1517].

Once calculated, the GRR can reflect the increased predisposition risk on an individual with a specific CNR2-associated genotype to develop osteoporosis.

Thus, the present invention provides a method which can be used to predict predisposition of an individual to osteoporosis. The method is effected by obtaining a DNA sample from the individual. The DNA sample can be obtained from any source of cells of the individuals, including, but not limited to, peripheral blood cells (obtained using a syringe), skin cells (obtained from a skin biopsy), mouth epithelial cells (obtained from a mouth wash), and the like. Preferably, the DNA sample is obtained from a peripheral blood sample. Methods of extracting DNA from blood samples are well known in the art.

Once obtained, the DNA sample is preferably characterized for the presence or absence of at least one, preferably two, most preferably all three of the following osteoporosis-associated genotypes in the CNR2 locus: the C allele of SNP hCV79667, the A allele of SNP hCV11546265 and the G allele of SNP hCV515481.

The method can be also employed by characterizing the presence or absence of the G allele of SNP rs2502992 and/or the C allele of SNP rs2501432.

The term "absence" as used herein in regard to the genotype describes the negative result of a specific genotype determination test. For example, if the genotype determination test is suitable for the identification of cytosine nucleotide—containing allele of SNP hCV79667 (rs4649119) set forth in SEQ ID NO:11, and the individual on which the test is performed is homozygote for the guanine nucleotide—containing allele of SNP hCV79667 (rs4649119), then the result of the test will be "absence of genotype".

The SNPs of the present invention can be identified using a variety of approaches suitable for identifying sequence alterations. One option is to determine the entire gene sequence of a PCR reaction product. Alternatively, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

Following is a non-limiting list of SNPs detection methods which can be used to identify one or more of the SNPs described above.

Restriction fragment length polymorphism (RFLP): This method uses a change in a single nucleotide (the SNP nucleotide) which modifies a recognition site for a restriction enzyme resulting in the creation or destruction of an RFLP. Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807-6817, 1990). However, this method requires the use of osmium tetroxide and piperidine, two highly noxious chemicals which are not suited for use in a clinical laboratory.

Allele specific oligonucleotide (ASO): In this method, an allele-specific oligonucleotide (ASO) is designed to hybridize in proximity to the polymorphic nucleotide, such that a primer extension or ligation event can be used as the indicator of a match or a mismatch. Hybridization with radioactively labeled allelic specific oligonucleotides (ASO) also has been applied to the detection of specific SNPs (Conner et al., Proc. Natl. Acad. Sci., 80:278-282, 1983). The method is based on the differences in the melting temperature of short DNA fragments differing by a single nucleotide. Stringent hybridization and washing conditions can differentiate between mutant and wild-type alleles.

Denaturing/Temperature Gradient Gel Electrophoresis (DGGE/TGGE): Two other methods rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can detect the presence of SNPs in the target sequences because of the corresponding changes in their electrophoretic mobilities. The fragments to be analyzed, usually PCR products, are "clamped" at one end by a long stretch of G-C base pairs (30-80) to allow complete denaturation of the sequence of interest without complete dissociation of the strands. The attachment of a GC "clamp" to the DNA fragments increases the fraction of mutations that can be recognized by DGGE (Abrams et al., Genomics 7:463-475, 1990). Attaching a GC clamp to one primer is critical to ensure that the amplified sequence has a low dissociation temperature (Sheffield et al., Proc. Natl. Acad. Sci., 86:232-236, 1989; and Lerman and Silverstein, Meth. Enzymol., 155:482-501, 1987). Modifications of the technique have been developed, using temperature gradients (Wartell et al., Nucl. Acids Res., 18:2699-2701, 1990), and the method can be also applied to RNA:RNA duplexes (Smith et al., Genomics 3:217-223, 1988).

Limitations on the utility of DGGE include the requirement that the denaturing conditions must be optimized for each type of DNA to be tested. Furthermore, the method requires specialized equipment to prepare the gels and maintain the needed high temperatures during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE) (Borrensen et al., Proc. Natl. Acad. Sci. USA 88:8405, 1991). CDGE requires that gels be performed under different denaturant conditions in order to reach high efficiency for the detection of SNPs.

A technique analogous to DGGE, termed temperature gradient gel electrophoresis (TGGE), uses a thermal gradient rather than a chemical denaturant gradient (Scholz, et al., Hum. Mol. Genet. 2:2155, 1993). TGGE requires the use of specialized equipment which can generate a temperature gradient perpendicularly oriented relative to the electrical field. TGGE can detect mutations in relatively small fragments of DNA therefore scanning of large gene segments requires the use of multiple PCR products prior to running the gel.

Single-Strand Conformation Polymorphism (SSCP): Another common method, called "Single-Strand Conformation Polymorphism" (SSCP) was developed by Hayashi, Sekya and colleagues (reviewed by Hayashi, PCR Meth. Appl., 1:34-38, 1991) and is based on the observation that single strands of nucleic acid can take on characteristic conformations in non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations (Orita, et al., Genomics 5:874-879, 1989).

The SSCP process involves denaturing a DNA segment (e.g., a PCR product) that is labeled on both strands, followed by slow electrophoretic separation on a non-denaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

Dideoxy fingerprinting (ddF): The dideoxy fingerprinting (ddF) is another technique developed to scan genes for the presence of mutations (Liu and Sommer, PCR Methods Appli., 4:97, 1994). The ddF technique combines components of Sanger dideoxy sequencing with SSCP. A dideoxy sequencing reaction is performed using one dideoxy terminator and then the reaction products are electrophoresed on nondenaturing polyacrylamide gels to detect alteration in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200-300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion sub-cloning or primer walking, in order to cover the entire fragment. SSCP and DGGE have even more severe size limitations. Because of reduced sensitivity to sequence changes, these methods arc not considered suitable for larger fragment. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

Pyrosequencing™ analysis (Pyrosequencing, Inc. Westborough, Mass., USA): This technique is based on the hybridization of a sequencing primer to a single stranded, PCR-amplified, DNA template in the presence of DNA polymerase, ATP sulfurylase, luciferase and apyrase enzymes and the adenosine 5' phosphosulfate (APS) and luciferin substrates. In the second step the first of four deoxynucleotide triphosphates (dCNTP) is added to the reaction and the DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. In the last step the ATP sulfurylase quantitatively converts PPi to ATP in the presence of adenosine 5 phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a pyrogram™. Each light signal is proportional to the number of nucleotides incorporated.

Acycloprime™ analysis (Perkin Elmer, Boston, Mass., USA): This technique is based on fluorescent polarization (FP) detection. Following PCR amplification of the sequence containing the SNP of interest, excess primer and dNTPs are removed through incubation with shrimp alkaline phosphatase (SAP) and exonuclease I. Once the enzymes arc heat inactivated, the Acycloprime-FP process uses a thermostable polymerase to add one of two fluorescent terminators to a primer that ends immediately upstream of the SNP site. The terminator(s) added are identified by their increased FP and represent the allele(s) present in the original DNA sample. The Acycloprime process uses AcycloPol™, a novel mutant thermostable polymerase from the Archeon family, and a pair of AcycloTerminators™ labeled with R110 and TAMRA, representing the possible alleles for the SNP of interest. AcycloTerminator™ non-nucleotide analogs are biologically active with a variety of DNA polymerases. Similarly to 2',3'-dideoxynucleotide-5'-triphosphates, the acyclic analogs function as chain terminators. The analog is incorporated by the DNA polymerase in a base-specific manner onto the 3'-end of the DNA chain, and since there is no 3'-hydroxyl, is unable to function in further chain elongation. It has been found that AcycloPol has a higher affinity and specificity for derivatized AcycloTerminators than various Taq mutant have for derivatized 2',3'-dideoxynucleotide terminators.

Reverse dot blot: This technique uses labeled sequence specific oligonucleotide probes and unlabeled nucleic acid samples. Activated primary amine-conjugated oligonucleotides are covalently attached to carboxylated nylon membranes. After hybridization and washing, the labeled probe, or a labeled fragment of the probe, can be released using oligomer restriction, i.e., the digestion of the duplex hybrid with a restriction enzyme. Circular spots or lines are visualized colorimetrically after hybridization through the use of streptavidin horseradish peroxidase incubation followed by development using tetramethylbenzidine and hydrogen peroxide, or via chemiluminescence after incubation with avidin alkaline phosphatase conjugate and a luminous substrate susceptible to enzyme activation, such as CSPD, followed by exposure to x-ray film.

It will be appreciated that advances in the field of SNP detection have provided additional accurate, easy, and inexpensive large-scale SNP genotyping techniques, such as dynamic allele-specific hybridization (DASH, Howell, W. M. et al., 1999. Dynamic allele-specific hybridization (DASH). Nat. Biotechnol. 17: 87-8), microplate array diagonal gel electrophoresis [MADGE, Day, I. N. et al., 1995. High-throughput genotyping using horizontal polyacrylamide gels with wells arranged for microplate array diagonal gel electrophoresis (MADGE). Biotechniques. 19: 830-5], the TaqMan system (Holland, P. M. et al., 1991. Detection of specific polymerase chain reaction product by utilizing the 5'→3' exonuclease activity of *Thermus aquaticus* DNA polymerase. Proc Natl Acad Sci USA. 88: 7276-80), as well as various DNA "chip" technologies such as the GeneChip microarrays (e.g., Affymetrix SNP chips) which are disclosed in U.S. Pat. No. 6,300,063 to Lipshutz, et al. 2001, which is fully incorporated herein by reference, Genetic Bit Analysis (GBA™) which is described by Goelet, P. et al. (PCT Appl. No. 92/15712), peptide nucleic acid (PNA, Ren B, et al., 2004. Nucleic Acids Res. 32: e42) and locked nucleic acids (LNA, Latorra D, et al., 2003. Hum. Mutat. 22: 79-85) probes, Molecular Beacons (Abravaya K, et al., 2003. Clin Chem Lab Med. 41: 468-74), intercalating dye [Germer, S. and Higuchi, R. Single-tube genotyping without oligonucleotide probes. Genome Res. 9:72-78 (1999)], FRET primers (Solinas A et al. 2001. Nucleic Acids Res. 29: E96), AlphaScreen (Beaudet L, et al., Genome Res. 2001, 11(4): 600-8), SNPstream (Bell P A, et al., 2002. Biotechniques. Suppl.: 70-2, 74, 76-7), Multiplex minisequencing (Curcio M, et al., 2002. Electrophoresis. 23: 1467-72), SnaPshot (Turner D, et al., 2002. Hum Immunol. 63: 508-13), MassEXTEND (Cashman J R, et al., 2001. Drug Metab Dispos. 29: 1629-37), GOOD assay (Sauer S, and Gut I G. 2003. Rapid Commun. Mass. Spectrum. 17: 1265-72), Microarray minisequencing (Liljedahl U, et al., 2003. Pharmacogenetics. 13: 7-17), arrayed primer extension (APEX) (Tonisson N, et al., 2000. Clin. Chem. Lab. Med. 38: 165-70), Microarray primer extension (O'Meara D, et al., 2002. Nucleic Acids Res. 30: e75), Tag arrays (Fan J B, et al., 2000. Genome Res. 10: 853-60), Template-directed incorporation (TDI) (Akula N, et al., 2002. Biotechniques. 32: 1072-8), fluorescence polarization (Hsu T M, et al., 2001. Biotechniques. 31: 560, 562, 564-8), Colorimetric oligonucleotide ligation assay (OLA, Nickerson D A, et al., 1990. Proc. Natl. Acad. Sci. USA. 87: 8923-7), Sequence-coded OLA (Gasparini P, et al., 1999. J. Med. Screen. 6: 67-9), Microarray ligation, Ligase chain reaction, Padlock probes, Rolling circle amplification, Invader assay (reviewed in Shi MM-2001. Enabling large-scale pharmacogenetic studies by high-throughput mutation detection and genotyping technologies. Clin Chem. 47: 164-72), coded microspheres (Rao K V et al., 2003. Nucleic Acids Res. 31: e66) and MassArray (Leushner J. Chiu N H, 2000. Mol Diagn. 5: 341-80).

For example, as is shown in Examples 3 of the Examples section which follows, for the determination of specific alleles of SNPs hCV79667, hCV11546265 and hCV515481 the TaqMan C 79667, C 11546265, and C 515481 Assays-On-Demand™ (Applied Biosystems) kits were employed. These kits include two unlabeled specific PCR primers of each SNP and one FAM™ dyc-labeled TaqMan® MGB probe capable of determining the presence of a specific allele of each SNP.

As is mentioned before, the Gln63Arg missense mutation was also associated by the present inventors to osteoporosis. It will be appreciated that missense mutations can modulate protein properties (e.g., membrane solubility, protein folding) which may affect protein expression and activity. Since the Gln63Arg missense mutation is located between the first and second transmembrane portions of the CB2 receptor, such a mutation can result in an abnormal activity of the CB2 receptor, and thus may lead to osteoporosis. Additionally or alternatively, such a missense mutation can together with another, yet-to-be-found mutation, reduce the activity or ligand binding capacity of the CB2 receptor and thus lead to osteoporosis. These results therefore suggest the use of the presence or absence of the Gln63Arg missense mutation in determining predisposition to osteoporosis.

Thus, according to another aspect of the present invention there is provided a method of determining if an individual is predisposed to osteoporosis. The method is effected by obtaining a CB2 protein-containing biological sample from the individual, identifying the presence or absence of an Arginine polymorph at position 63 of the CB2 protein set forth in SEQ ID NO:26 (NP_001832) from the CB2 protein—containing biological sample, wherein presence indicates increased predisposition risk to osteoporosis.

The CB2-containing biological sample utilized by the present invention can be for example, peripheral blood cells, bone marrow cells, lymph nodes cells, cartilage, uterine cells, placenta cells, reproductive fluid cells, intestinal mucosal cells present in feces, muscle cells, skin cells, buccal cells, cells present in saliva, cells present in sweats, and the like. Such samples can be collected using effusions, scrapes, fine needle aspirates, peripheral blood scrapings, paraffin embedded tissues, frozen sections and the like.

Determination of the CB2 Gln63Arg amino acid change can be accomplished directly, by analyzing the protein gene products of the CNR2 gene, or portions thereof. Such a direct analysis is often accomplished using an immunological detection method.

Immunological detection methods: The immunological detection methods used in context of the present invention are fully explained in, for example, "Using Antibodies: A Laboratory Manual" [Ed. Harlow, David Lane eds., Cold Spring Harbor Laboratory Press (1999)] and those familiar with the art will be capable of implementing the various techniques summarized hereinbelow as part of the present invention. All of the immunological techniques require antibodies specific to at least one of the two CB2 alleles. Immunological detection methods suited for use as part of the present invention include, but are not limited to, radio-immunoassay (RIA), enzyme linked immunosorbent assay (ELISA), western blot, immunohistochemical analysis, and fluorescence activated cell sorting (FACS).

Radio-immunoassay (RIA): In one version, this method involves precipitation of the desired substrate, CB2 in this case and in the methods detailed hereinbelow, with a specific antibody and radiolabelled antibody binding protein (e.g., protein A labeled with $I^{125}$) immobilized on a precipitable carrier such as agarose beads. The number of counts in the precipitated pellet is proportional to the amount of substrate. In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme linked immunosorbent assay (ELISA): This method involves fixation of a sample (e.g., fixed cells or a proteinaceous solution) containing a protein substrate to a surface such as a well of a microliter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabelled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Immunohistochemical analysis: This method involves detection of a substrate in situ in fixed cells by substrate specific antibodies. The substrate specific antibodies may be enzyme linked or linked to fluorophores. Detection is by microscopy and subjective evaluation. If enzyme linked antibodies are employed, a calorimetric reaction may be required.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

It will be appreciated by one ordinarily skilled in the art that determining the CB2 phenotype of an individual, either directly (e.g., by detecting the protein polymorphs) or genetically (e.g., by detecting the presence or absence of SNP genotypes), may be effected using any suitable biological sample derived from the examined individual, including, but not limited to, blood, plasma, blood cells, saliva or cells derived by mouth wash, and body secretions such as urine and tears, and from biopsies, etc. Alternatively, nucleic acid tests can be performed on dry samples (e.g. hair or skin). The sample may contain genomic DNA, cDNA or RNA. Methods of preparing genomic DNA or cDNA and RNA are well known in the art.

The antibody used in the method of the present invention is selected differentially interactable with at least one form of a CB2 protein encoded by a CB2 allele having an SNP rs2502992 or an SNP rs2501432, and can differentiate between polymorphs of the CB2 protein via differential antibody interaction. Antibodies useful in context of this embodiment of the invention can be prepared using methods of antibody preparation well known to one of ordinary skills in the art, using, for example, synthetic peptides derived from the two different forms of the CB2 protein for vaccination of antibody producing animals and subsequent isolation of antibodies therefrom. Monoclonal antibodies specific to each of the CB2 variants can also be prepared as is described, for example, in "Current Protocols in Immunology" Volumes I-III Coligan J. E., Ed. (1994); Stites et al. (Eds), "Basic and Clinical Immunology" (8th Edition), Appleton & Lange, Norwalk, Conn. (1994); Mishell and Shiigi (Eds), "Selected Methods in Cellular Immunology", W. H. Freeman and Co., New York (1980).

The term "antibody" as used in the present invention includes intact molecules as well as functional fragments thereof, such as Fab, F(ab')$_2$, and Fv that are capable of binding to macrophages. These functional antibody fragments are defined as follows: Fab, the fragment which contains a monovalent antigen-binding fragment of an antibody molecule, can be produced by digestion of whole antibody with the enzyme papain to yield an intact light chain and a portion of one heavy chain; Fab', the fragment of an antibody molecule that can be obtained by treating whole antibody with pepsin, followed by reduction, to yield an intact light chain and a portion of the heavy chain; two Fab' fragments are obtained per antibody molecule; (Fab')$_2$, the fragment of the antibody that can be obtained by treating whole antibody with the enzyme pepsin without subsequent reduction; F(ab')$_2$ is a dimer of two Fab' fragments held together by two disulfide bonds; Fv, defined as a genetically engineered fragment containing the variable region of the light chain and the variable region of the heavy chain expressed as two chains; and single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. See for example, Harlow and Lane, Antibodies: A. Laboratory Manual, Cold Spring Harbor Laboratory, New York, 1988, incorporated herein by reference.

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as gluteraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

It will be appreciated that the reagents utilized by the methods for determining predisposition to osteoporosis according to the present invention and which are described hereinabove can form a part of a kit.

Such a kit includes at least one reagent for determining a presence or absence in a homozygous or heterozygous form, of at least one osteoporosis-associated genotype in the CNR2 locus or in neighboring loci which are in linkage disequilibrium with the CNR2 loci.

According to preferred embodiments the kit further comprising packaging material packaging at least one reagent and a notification in or on the packaging material. Such a notification identifies the kit for use in determining if an individual is predisposed to osteoporosis.

The kit also includes the appropriate instructions for use and labels indicating FDA approval for use in vitro.

The methods and kits of determining predisposition of an individual to osteoporosis according to the present invention can be used in genetic counseling, prior to making a decision to conceive a child and in a routine check-up of young children and adolescents, in order to provide with individuals at risk with guidelines for preventing future osteoporosis by, for example, increasing bone mass via physical exercising and life style. In addition, such methods can be used in adults, especially in women before menopause, in order to provide than with suitable treatment prior to the deterioration of bone tissue.

It will be appreciated that the genotypes and the polymorphs of the SNPs from the CNR2 locus can be used to assist in diagnosing osteoporosis in individuals who are suspected of having osteoporosis, based on low bone mineral density or a tendency of bone fractures.

Thus, according to another aspect of the present invention there is provided a method of improving diagnosis of osteoporosis in an individual.

As used herein, the phrase "improving diagnosis" refers to assisting in the diagnosis of osteoporosis, wherein "diagnosis" means the determination of the existence of a disease, which generally involves the evaluation of a patients medical history, clinical symptoms and laboratory test results.

Such diagnosis would be effected as described above in individuals who are suspected of having osteoporosis. For example, if a post-menopause woman breaks the hip bone during a non-intensive task such as walking, she might be suffering from a deterioration of the bone structure, a phenomena characteristics of osteoporosis Thus, such a woman is suspected of having osteoporosis.

Since the present inventors have shown that mutations in the CNR2 locus are highly associative with osteoporosis, and since this locus includes the CB2 gene which encodes a receptor participating in bone growth/repair regulation (see Examples 1 and 2 of the Examples section which follows and PCT IL/03/00480), it is highly likely that this chromosomal region includes osteoporosis-causing genetic mutations, which can serve as targets for osteoporosis treatment Thus, according to another aspect of the present invention there is provided a method of identifying a putative osteoporosis-causing genetic mutation in a subject.

As used herein, the phrase "putative osteoporosis-causing genetic mutation" refers to a mutation, i.e. a nucleic acid substitution, which is suspected of causing osteoporosis.

Thus, according to preferred embodiments of the present invention, the method is effected by identifying at least one nucleic acid change in a coding or regulatory nucleic acid sequence being: (a) within a chromosomal sequence region encompassed by SNP hCV79667 and SNP rs2501432, or (b) being in linkage to the chromosomal sequence region, thereby identifying the putative osteoporosis-causing genetic mutation in the subject.

Methods and reagents for identifying nucleic acid changes are fully described hereinabove in the context of determining a genotype of a specific SNP.

As used herein, the phrase "nucleic acid substitution" refers to any mutation in the DNA sequence of an individual which can lead to osteoporosis. Non-limiting examples of such nucleic acid changes include a missense mutation (i.e., a mutation which changes an amino acid residue in the protein with another amino acid residue), a nonsense mutation (i.e., a mutation which introduces a stop codon in a protein), a frameshift mutation (i.e., a mutation, usually, deletion or insertion of nucleic acids which changes the reading frame of the protein, and may result in an early termination or in a longer amino acid sequence), a readthrough mutation (i.e., a mutation which results in an elongated protein due to a change in a coding frame or a modified stop codon), a promoter mutation (i.e., a mutation in a promoter sequence, usually 5' to the transcription start site of a gene, which result in up-regulation or down-regulation of a specific gene product), a regulatory mutation (i.e., a mutation in a region upstream or downstream, or within a gene, which affects the expression of the gene product), a deletion (i.e., a mutation which deletes coding or non-coding nucleic acids in a gene sequence), an insertion (i.e., a mutation which inserts coding or non-coding nucleic acids into a gene sequence), an inversion (i.e., a mutation which results in an inverted coding or non-coding sequence), and a duplication (i.e., a mutation which results in a duplicated coding or non-coding sequence).

Such a putative mutation can be found, for example, on the sequence of 127 kb around the CNR2 locus, which is provided in the file "hCB2 127 kb 1strand.txt" and is incorporated herein. In addition, such a mutation can be one of the SNPs listed in the files "SNPs on 127 kb hCB2 seq.txt" and "all-SNPs-CNR2_context.txt", which are incorporated herein.

Table 1, hereinbelow, summarizes the location of the putative functional sequences of the CB2 receptor genomic sequence.

TABLE 1

Functional regions on the CB2 receptor genomic sequence

| Function | Begin bp in sequence | End bp in sequence |
| --- | --- | --- |
| Promoter 1 | 115111 | 114195 |
| Promoter 2 | 57996 | 57995 |
| Exon 1/5' UTR | 68275 | 68194 |
| Exon 2 | 30611 | 29027 |
| coding region of Exon 2 | 30566 | 29542 |

Table 1: The position of the functional regions on the CB2 genomic sequence are provided;
bp = base pair;
UTR = untranslated region.
Sequence numbers relate to location on the sequence provided in the file "hCB2 127 kb 1strand.txt".

Once an osteoporosis causing mutation is identified using the teachings of the present invention it can be used in determining predisposition and improving the diagnosis of osteoporosis in individuals. Moreover, the osteoporosis causing mutation(s) can be used as a target to screen and develop drugs which will correct the mutation by, for example, inducing the action of a deficient protein or inhibit over-expression of a constantly active protein. Thus, the teachings of the present invention can be used to develop specific drugs or agents capable of treating, preventing or delaying onset of osteoporosis.

For example, if the osteoporosis-causing mutation is a missense mutation in the cannabinoid binding site, resulting in low or no activation of the CB2 receptor, a possible treatment regimen would be to identify CB2 agonists capable of activating the mutated receptor. Possible agonists can be tested using cells expressing the CB2 receptor, such as bone marrow cells, muscle cells, COS cells and the like, which are transfected with an expression vector containing a nucleic acid sequence of the CB2 mRNA (GenBank Accession No. NM_001841). Non-limiting examples of such agonists include the BAY 38-7271 (Mauler, F., et al., CNS Drug Rev. 2003, 9: 343-58), HU-210 (McKallip, R. J., et al., Blood. 2002, 100: 627-34), and JTE-907 (Iwamura, H., et al., J. Pharmacol. Exp. Ther. 2001, 296: 420-5).

On the other hand, if the osteoporosis-causing mutation is a regulatory mutation in the CB2 promoter region, promoter activating agents can be tested in an in vitro system in which the expression of the CB2 mRNA is followed using a reporter gene such as the green fluorescent protein (GFP) which is ligated at the 3' end of the CB2 mRNA sequence.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828, 4,683, 202; 4,801,531; 5,192,659 and 5,272,057; "Cell Biology: A Laboratory Handbook", Volumes I-III Cellis, J. E., Ed. (1994); "Culture of Animal Cells-A Manual of Basic Technique" by Freshney, Wiley-Liss, N.Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); "Approaches to Gene Mapping in Complex human Diseases" Jonathan L. Haines and Margaret A. Pericak-Vance eds., Wiley-Liss (1998); "Genetic Dissection of Complex Traits" D. C. Rao and Michael A. Province eds., Academic Press (1999); "Introduction to Quantitative Genetics" D. S. Falconer and Trudy F. C. Mackay, Addison Wesley Longman Limited (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

CB2 Knock-Out Mice Display Characteristic Phenotypes of Osteoporosis

Cannabinoids exert their action via CB1 and CB2 receptors (Matsuda, L. A., et al., 1990, Nature, 346: 561-564; Munro, S., et al., 1993, Nature 365: 61-65). These receptors belong to the G-protein superfamily of coupled receptors exerting their biological actions by modulating adenylate cyclase and $Ca^{+2}$ and $K^+$ currents. CB1 receptors are present mostly in nervous system [Devane et al., Mol. Pharmacol. 34:605-613 (1988); Matsuda et al., Nature 346:561-564 (1990)] but also in some peripheral tissues [Shire et al., J. Biol. Chem. 270:3726-3731 (1995); Ishac et al., Br. J. Pharmacol. 118:2023-2028 (1996)]. On the other hand, CB2 receptors are present on macrophages in the spleen [Munro et al., Nature 365:61-65 (1993)] and are believed to have peripheral effects related to bronchial constriction, immunomodulation and inflammation. Other types or subtypes of cannabinoid receptors have been recently described, designated CB1-like receptors, CB2-like receptors, and non-CB1 non-CB2 receptors [Hanus et al., J. Pharmacol. Exper. Therapeutics 54: 161-202 (2002)].

International patent application PCT IL/03/00480 illustrates a substantial disruption of the trabecular structural integrity with possible severe consequences to the bone load bearing capacity in mice lacking the CB1 receptor gene (CNR1), suggesting a possible involvement of this receptor in bone stability and osteoporosis. To assess the potential role of CB2 in bone stability, the expression pattern of CB2 was evaluated in osteoblast and osteoclast cells.

Materials and Experimental Methods $CB2^{-/-}$ mice—Mice with a deletion of the CNR2 gene ($CB2^{-/-}$ mice) [Buckley, N. E., et al. Immunomodulation by cannabinoids is absent in mice deficient for the cannabinoid CB(2) receptor. Eur. J. Pharmacol. 396: 141-149 (2000)] were crossed for 10 generations to wild type C57BL/6J mice to generate a congenic C57BL/6J-$CB2^{-/-}$ strain.

Ovariectomy (OVX) mice—C3H mice (Harlan, Israel) were subjected to an ovariectomy procedure. HU-308 was synthesized as described before [Hanus, L., et al. HU-308: a specific agonist for CB(2), a peripheral cannabinoid receptor. Proc. Natl. Acad. Sci. U.S.A. 96: 14228-142-33 (1999)] and was daily injected once subcutaneously as an ethanol/emulphor/saline (1:1:18) solution.

All reported animals received calcein flurochrome (Sigma), 15 mg/Kg intraperitoneally four days and one day prior to sacrifice. Groups of 8-10 mice, 8-11 weeks old, were used in each experiment The experimental protocols were approved by the Institutional Animal Care and Use Committee, Faculty of Medicine, the Hebrew University of Jerusalem, Israel and by the Regierungspräsidium Köln for the University of Bonn, Germany.

Micro-computed tomography (µCT)—Whole femora were examined by µCT 40 (Scanco Medical, Bassersdorf, Switzerland). Scans were performed at a 20 µm resolution and images stored in 3-D arrays with 20 µm isotropic voxel size. Mineralized bone was differentially segmented by a global thresholding procedure [Müller, R & Rüegsegger, P. Micro-tomographic imaging for the nondestructive evaluation of trabecular bone architecture. Stud. Health Technol. Inform. 40: 61-79 (1997); Hildebrand, T., et al., Direct three-dimensional morphometric analysis of human cancellous bone microstructural data from spine, femur, iliac crest, and calcaneus. J. Bone Miner. Res. 14: 1167-1174 (1999)]. Trabecular bone parameters were measured in a metaphyseal segment, extending proximally from the proximal tip of the primary spongiosa to the proximal border of the distal femoral quartile. Cortical bone parameters were determined in a diaphyseal segment extending 1.12 mm distally from the midpoint between the femoral ends.

Histomorphometry and immunohistochemistry—After µCT image acquisition, the specimens were embedded undecalcified in Technovit 9100 (Heracus Kulzer, Wehrheim, Germany). Longitudinal sections through the mid-frontal plane were left unstained for dynamic histomorphometry based on the vital calcein double labelling. To identify osteoclasts, consecutive sections were stained for TRAP [Erlebacher, A & Derynck, R. Increased expression of TG F-beta 2 in osteoblasts results in an osteoporosis-like phenotype. J. Cell Biol 132: 195-210 (1996)]. Parameters were determined according to a standardized nomenclature [Parfitt, A. M., et al. Bone histomorphometry: standardization of nomenclature, symbols, and units. Report of the ASBMR Histomorphometry Nomenclature Committee. J. Bone Miner. Res. 2: 595-610 (1987)]. Immunohistochemistry was performed using paraffin-embedded decalcified sections (Ausubel, F. M. Current Protocols in Molecular Biology. Wiley Interscience, New York, 1995) with a rabbit anti-human polyclonal first antibody (Cayman Chemical, Ann Arbour, Mich., Cat. No. 101550).

Cell cultures and mRNA analysis—Osteoclastogenic cultures of monocytes derived from femora and tibiae of WT C57BL/6J mice were set as previously reported (Zou, W., et al., 2002. FASEB J. 16: 274-282). After separation and prior to RNA extraction or cell counts the cells were cultured for 5 days in medium containing M-CSF and RANKL (R&D Systems Inc. Minneapolis, Minn.). Primary bone marrow stromal cell cultures from femoral diaphyseal bone marrow and the MC3T3 E1 cells were cultured as reported previously (Frenkel, B., et al., 1997. Endocrinology 138: 2109-2116; Bab, I., et al., 1992. EMBO J. 11: 1867-1873). The cells were grown in osteogenic medium containing ascorbic acid, β-glycerophophate and dexamethasone (Frenkel, B., et al., 1997. Endocrinology 138: 2109-2116). RT-PCR was performed on random-primed cDNA using the PCR primers and conditions as listed in Table 2, hereinbelow.

TABLE 2

PCR primers and conditions

| Gene product (GenBank Accession number) | SEQ ID NOs. | Forward(F) and reverse(R) primers (5'-3') | Reaction Condition (Reference) | No. of PCR Cycles |
|---|---|---|---|---|
| CB1 (NM007726) | SEQ ID NO:1 SEQ ID NO:2 | F: TGGTGTATGATGTCTTTGGG K: ATGCTGGCTGTGTTATTGGC | Noe et al. Adv. Exp Med Biol. 437: 223-9, 1998; Noe et al. Adv. Exp. Med. Biol. 493: 215-21, 2001. | 40 cycles |
| CB2 (NM_001841) | SEQ ID NO:3 SEQ ID NO:4 | F: AACGGTGGCTTGGAGTTCAAC R: TAGGTAGCGGTCAACAGCGGTTAG | Lee et al. Eur. J. Pharmacol. 423; 235-41, 2001. | For monocytes and osteoclasts 26 cycles: for osteblasts 32 cycles. |
| TNSALP (J02980) | SEQ ID NO:5 SEQ ID NO:6 | F: GACA-CAAGCATTCCCACTAT R: ATCAG-CAGTAACCACAGTCA | Ohkuhn et al. Br J Pharmacol. 131: 1667-1672, 2000. | 25 cycles |
| PTHRc1 (NM_011199) | SEQ ID NO:7 SEQ ID NO:8 | F: CAAGAAGTGGATCATCCAGGT R: GCTGCTACTCCCACTTCGTGCTTT | Kato et al. Bone Min. Res. 16: 1622-1633, 2001. | 35 cycles |
| β-actin (NM_001101) | SEQ ID NO:9 SEQ ID NO:10 | F: GAGACCTTCAACACCCCAGCC R: GGCCATCTCTTGCTCGAAGTC | Annealing Temp. 62° C.; 1 mM $MgCl_2$ | 18 cycles |

Table 2: PCR primers and conditions used for RT-PCR reactions are presented. CB1 = Cannabinoid receptor 1; CB2 = Cannabinoid receptor 2; TNSALP = tissue non-specific alkaline phosphatase; PTHRc1 = parathyroid hormone receptor I.

In the cell count experiments, ligands were dissolved in dimethylsulfoxide and further diluted to their final concentration using tissue culture medium. For osteoclast counts the cultures were fixed in ethanol and TRAP-stained. Primary bone marrow derived osteoblast cultures were initially grown in osteogenic medium to allow for CB2 expression. The cells were then serum starved for 2 hours followed by 48 hours incubation in (α-MEM supplemented with 4% BSA and ligand. Cells were separated using chondroitinase and trypsin (Krebsbach, P. H., et al., 1998. Transplantation 66, 1272-1278) and counted with a hemocytometer in triplicate wells per condition.

Experimental Results

Figure 1B:
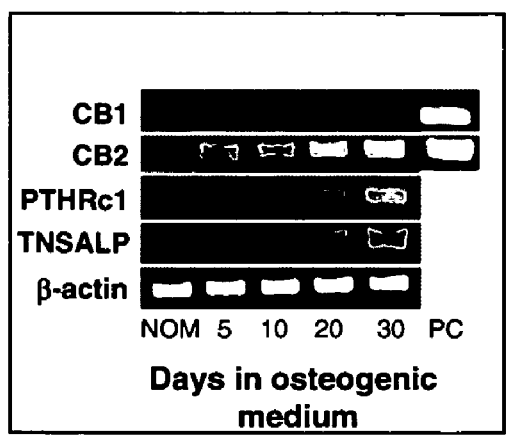

The expression level of CB2 increases with progression of osteoblastic differentiation—To assess a potential role for the endocannabinoid system in bone remodelling, the expression of the cannabinoid receptor was detected in mouse preosteoblastic cells whose osteoblastic differentiation was promoted using the osteogenic medium as described in Materials and Experimental Methods. As is shown in FIGS. 1a-b, while CB2 expression in preosteoblastic cells paralleled the expression of the osteoblastic marker genes TNSALP and PTHRc1, the expression of CB2 in stromal cells was detected from day 5 in culture and was stable throughout the culturing period. Noteworthy that CB2 mRNA was undetectable when the preosteoblastic cells were grown in non-osteogenic medium (FIG. 1a, NOM). In addition, the mRNA of the CB1 receptor was absent from cells cultured in either osteogenic or non-osteogenic medium (FIGS. 1a-b). These results demonstrate that the expression of CB2 receptors is dependent on osteoblast differentiation.

Figure 1C:
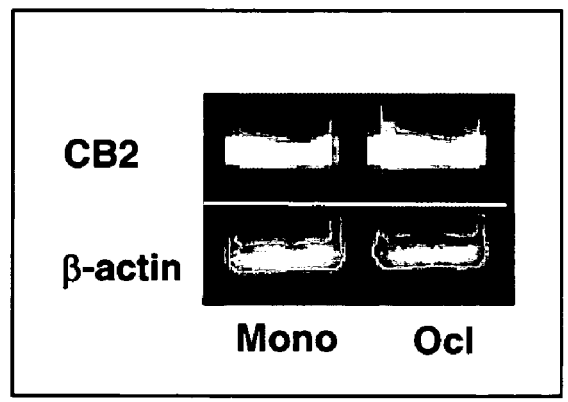

CB2 receptor mRNA is expressed in osteoclasts—Osteoclasts are derived from the monocyte-macrophage lineage which has been reported to express CB2 (Ross, R. A., et al., 2000. Bur. J. Pharmacol. 401: 121-130; Chang, Y. H., et al., 2001. J. Cell. Biochem. 81: 715-723 (2001). To analyse CB2 mRNA level in the osteoclast lineage, in vitro osteoclastogenesis was initiated and promoted in bone marrow derived monocyte culture by M-CSF and RANKL (Zou, W., et al., 2002. FASEB J. 16: 274-282). As is shown in FIG. 1c, CB2 mRNA transcripts were found in both bone marrow-derived osteoclasts and their monocytic progenitors. As in the osteoblastic cells, the mRNA of CB1 was undetected in cells of the osteoclast lineage (data not shown).

Figure 1E:
Figure 1D:
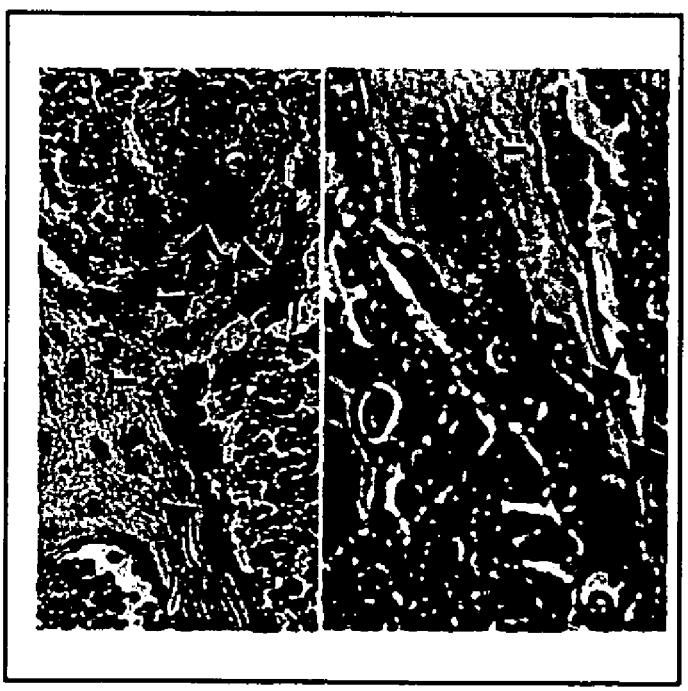

CB2 receptor protein is expressed in osteoblast, osteocyte and osteoclast cells—To further investigate the mode of CB2 expression in bone cells, immunohistochemistry analysis was performed on slides of the distal femoral metaphysis using specific anti-CB2 antibodies. As is shown in FIGS. 1d-e, CB2 receptors arc clearly expressed in osteoblasts, osteocytes and osteoclasts from wild-type mice (FIG. 1d) but not from CB2-deficient (FIG. 1e) mice.

Figure 1F:
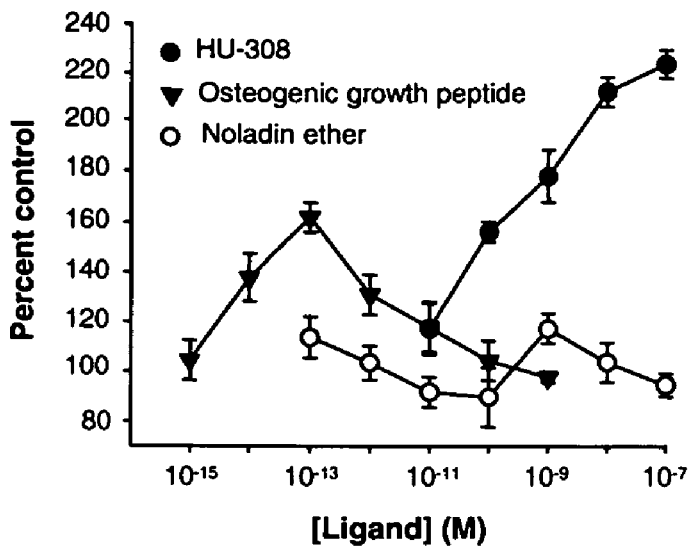

CB2 receptors on osteoblast cells are functional—The functionality of the bone cell CB2 receptors was assessed in preosteoblastic and osteoclastic culture systems using the HU-308, a CB2 specific agonist (Hanus, L., et al. 1999. HU-308: a specific agonist for CB(2), a peripheral cannabinoid receptor. Proc. Natl. Acad. Sci. U.S.A. 96: 14228-14233). As is shown in FIG. 1f, HU-308 elicited a potent increase in the number of diaphyseal bone marrow derived stromal cells which were grown for 10 days in osteogenic medium to allow for partial osteoblastic differentiation and hence, a significant level of CB2 expression On the other hand, Noladin ether, a specific CB1 against (Hanus, L., et al., 2001. 2-arachidonyl glyceryl ether, an endogenous agonist of the cannabinoid CB1 receptor. Proc. Natl. Acad. Sci. U.S.A. 98: 3662-3665) had no significant effect (FIG. 1f). In addition, the activity of the tissue non-specific alkaline phosphatase (TNSALP) was unaffected by the CB2 ligand; in the absence of matrix mineralization at this early differentiation stage, alizarin red S staining was negative in both control and cannabinoid treated cultures (data not shown). Thus, the HU-308-induced increase in cell number in this system is consistent with a direct CB2-mediated stimulation of preosteoblasts and implicates preosteoblastic cell pool expansion as a major mechanistic aspect of the endocannabinoid action in bone.

Figure 1G:
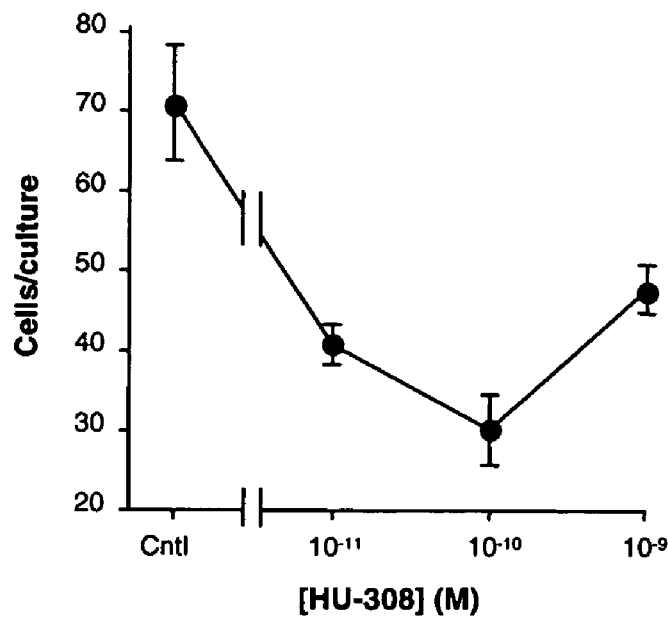

CB2 receptors restrain osteoclast differentiation—In the diaphyseal bone marrow derived osteoclastic cell system, HU-308 induced a marked dose dependent decrease in the number of TRAP positive multinucleated cells (FIG. 1g), suggesting a specific role for CB2 in restraining osteoclast differentiation.

These results demonstrate that CB2 signalling has a dual effect in bone, namely, the stimulation and inhibition of the osteoblast and osteoclast lineages, respectively.

Example 2

CB2$^{-/-}$ Mice Have Low Bone Mass and High Bone Turnover

To further substantiate the physiologic role of CB2 in bone remodelling, the skeletal phenotype of sexually mature mice with a deletion of the CB2 gene was characterized, as follows.

Materials and Methods—as in Example 1, hereinabove.

Experimental Results

Figure 2A:
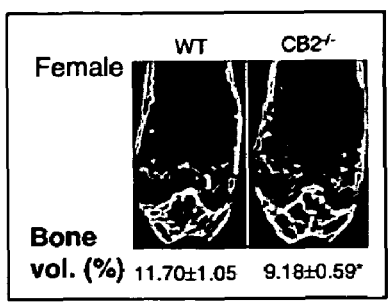
FIGS. 2a-k illustrate low trabecular bone mass/high bone turnover phenotype in $CB2^{-/-}$ mice.
Figure 2C:
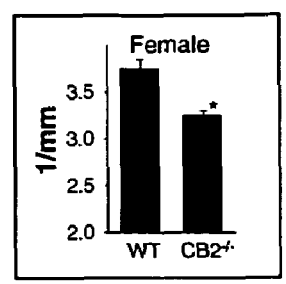
Figure 2E:
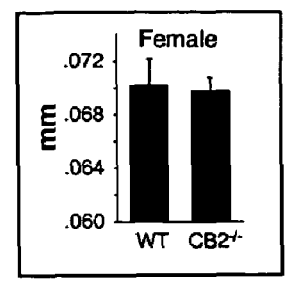
Figure 2B:
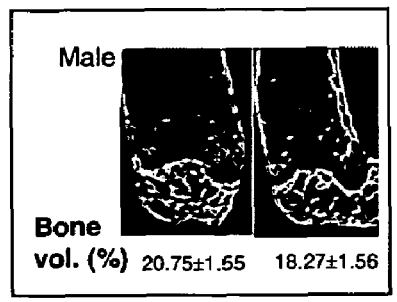
Figure 2D:
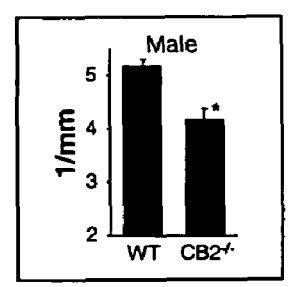
Figure 2F:
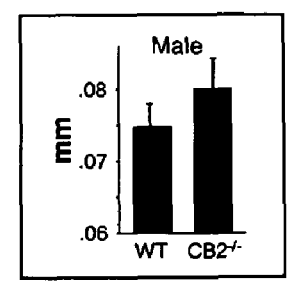

CB2$^{-/-}$ animals have lower trabecular bone mass—As is shown in FIGS. 2a-b, the trabecular bone volume of CB2$^{-/-}$ female and CB2$^{-/-}$ male mice was found to be approximately 22% and 12% lower, respectively, than that of wild-type animals. This decrease was attributable to a lower trabecular number (FIGS. 2c-d), but not to a reduced trabecular thickness (FIGS. 2e-f). Thus, these results demonstrate that CB2 deficient mice have lower bone mass, similarly to osteoporosis patients.

Figure 2G:
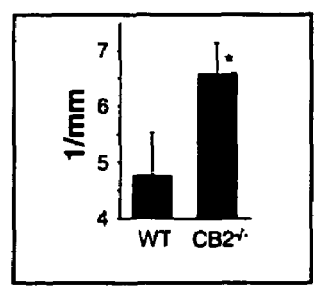
Figure 2H:
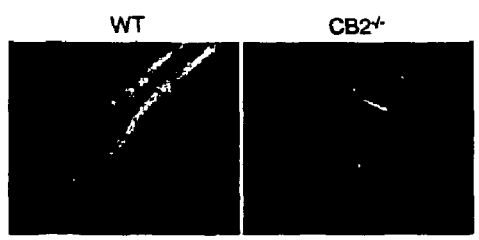
Figure 2I:
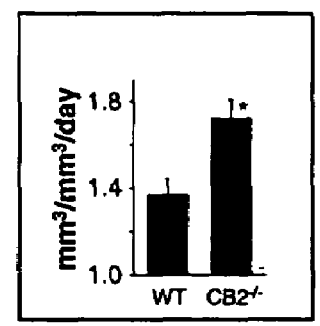
Figure 2J:
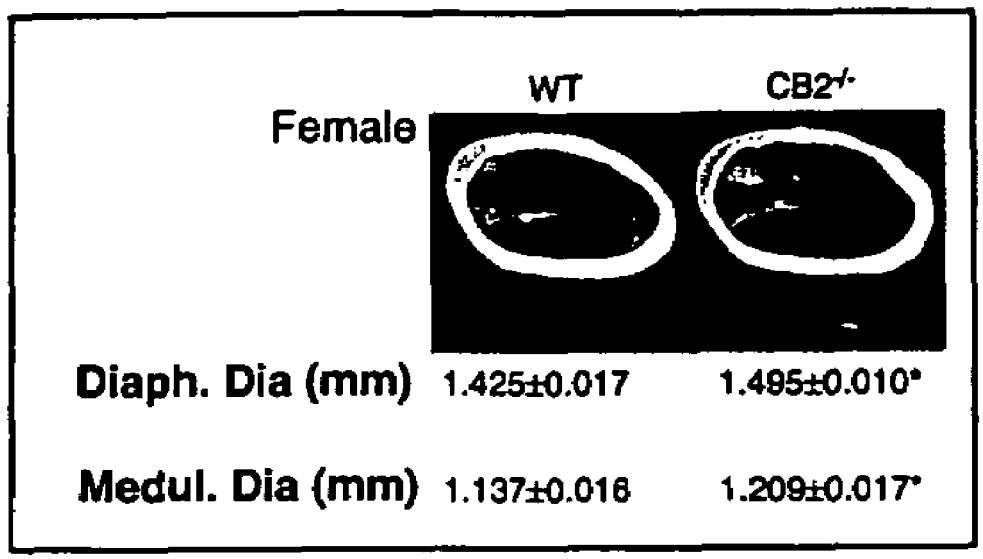
Figure 2K:
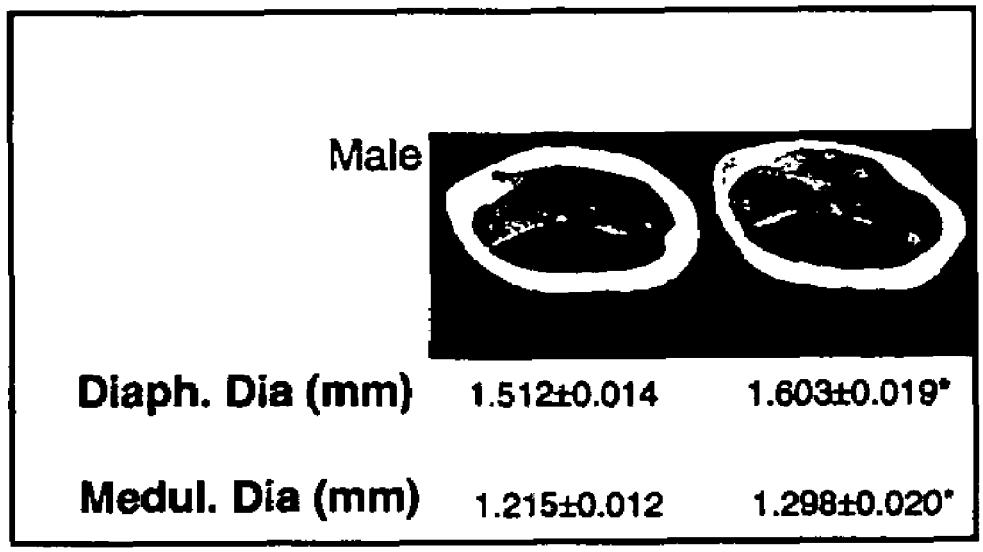
Figure 3:
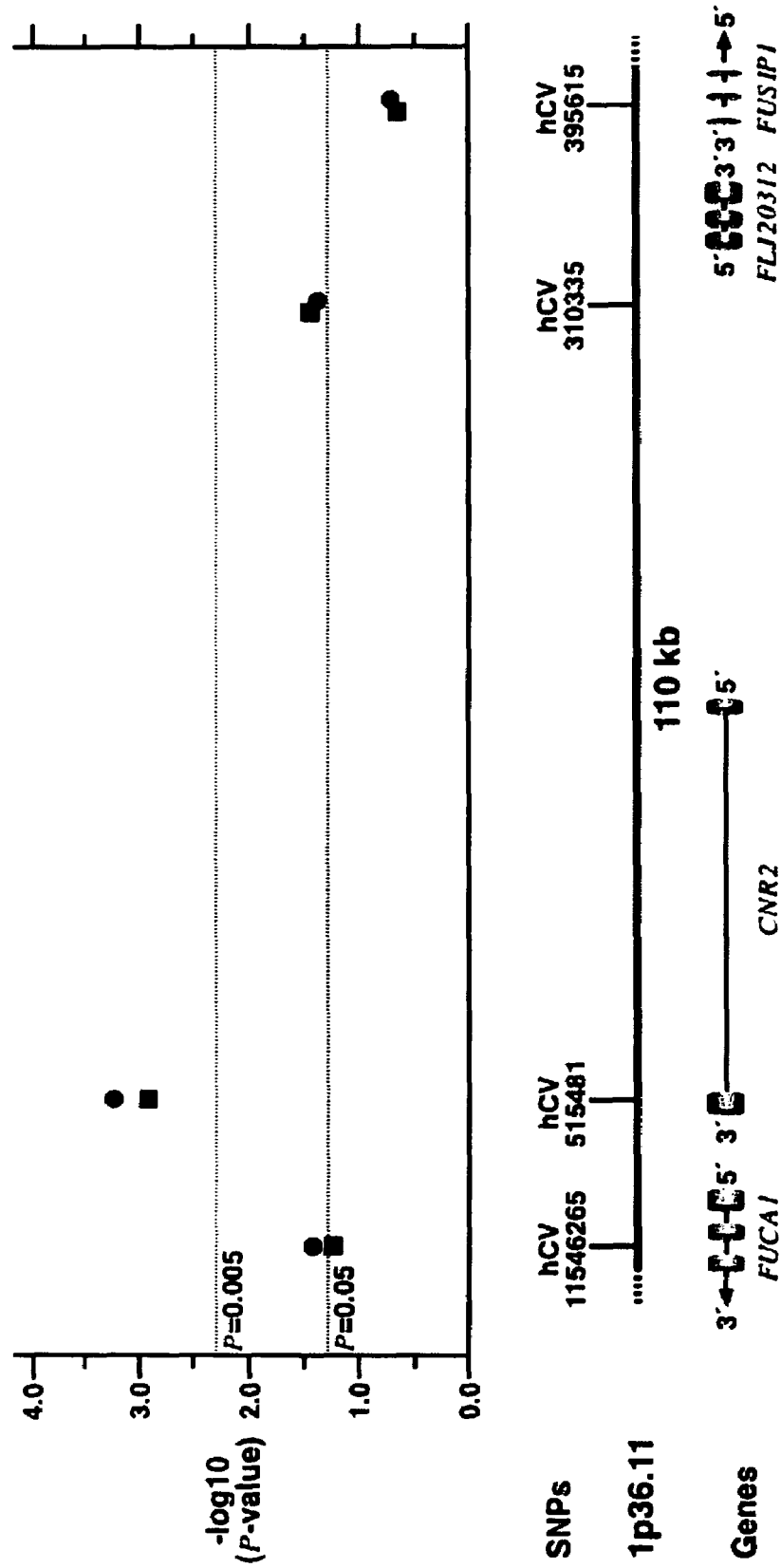
FIG. 3 is a schematic presentation of a region of 110 kb on human chromosome 1p36.11 including the location of selected single nucleotide polymorphisms (SNPs). Coloured slices=exons of the noted genes; Red boxes=p-values for allelic association; pink circles=p-values for genotypic association; FUCA1=alpha-L fucosidase; CNR2=cannabinoid receptor 2; FUSIP1=FUS interacting protein (serine-arginine rich) 1; FLJ20312=hypothetical protein FLJ35961 (Interim).
Figure 4A:
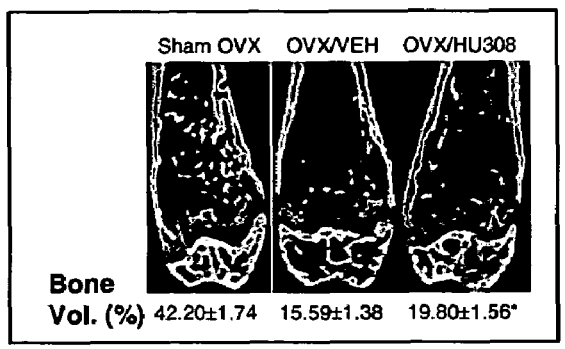
FIGS. 4a-g illustrate the effect of the CB2 specific agonist, HU-308, in attenuating ovariectomy (OVX)-induced femoral bone loss in sexually mature mice. OVX mice were injected for 4 weeks with either HU-308 at 10 mg/Kg/day (OVX/HU308) or vehicle (OVX/VEH) commenced at the time of operation, or were remained untreated (Sham OVX).
Figure 4B:
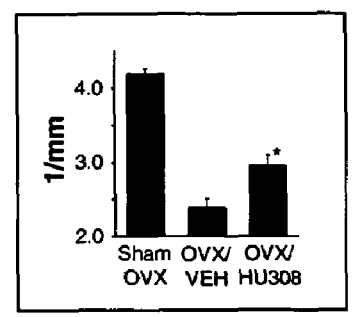
Figure 4C:
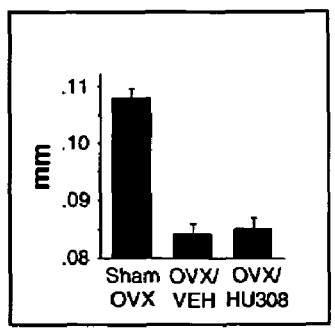
Figure 4D:
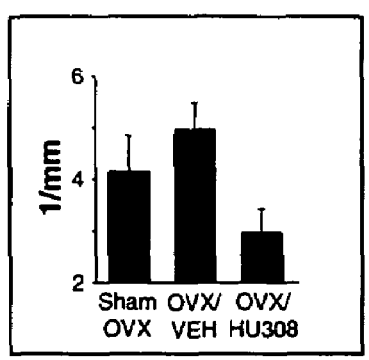
Figure 4E:
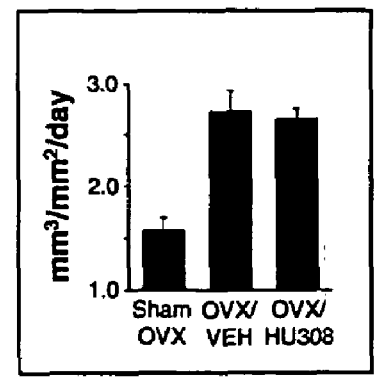
Figure 4F:
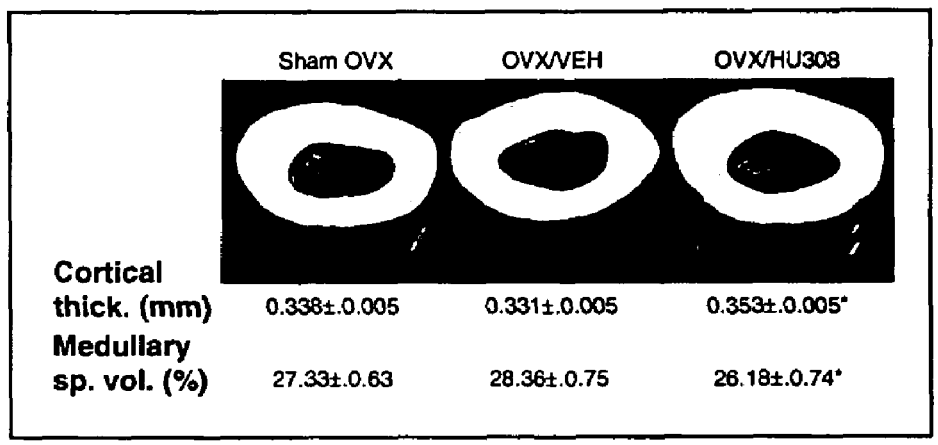
Figure 4G:
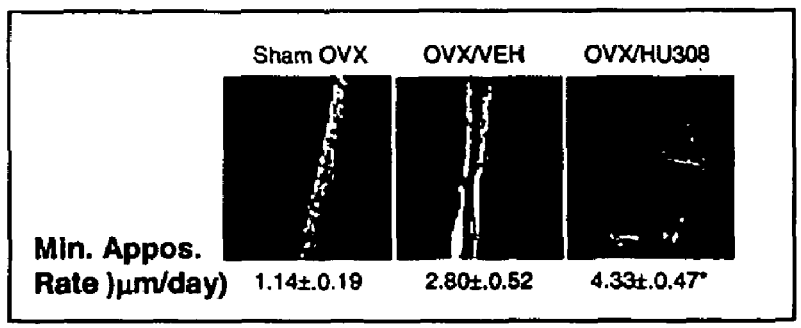

CB2$^{-/-}$ animals exhibit high bone turnover—To further substantiate the function of CB2 receptors in bone remodelling, the number of osteoclasts and the rate of bone formation were compared between CB2$^{-/-}$ and wild-type mice. As is shown in FIGS. 2g-i, both osteoclast number and the rate of bone formation were higher in CB2$^{-/-}$ mice (FIGS. 2d, 2e and 2f). These results indicate that the low bone mass (LBM) in these animals was associated with a high bone turnover, reminiscent of the high turnover bone loss in sex hormone depleted subjects (Manolagas, S. C., et al., 1995, Ciba Found. Symp. 191: 187-196). In addition, CB2$^{-/-}$ mice also showed increased diaphyseal diameter with unchanged cortical thickness (FIGS. 2g, j-k) a feature reminiscent of "cortical expansion" of human osteoporosis (Ammann, P. & Rizzoli, R. 2003 Bone strength and its determinants. Osteoporos, Int. 14 Suppl 3, S13-S18).

Analysis and discussion—Enhanced bone formation results primarily from increased osteoclastic activity and its coupling to osteoblastic activity (Rubin, J., et al., 2002. J. Clin. Endocrinol, Metab. 87: 4273-4279). Thus, bone formation may be amplified via resorption-stimulated pathways that compensate for the absence of CB2 signalling (Martin, T. J. 1993, Osteoporos. Int. 3 Suppl 1, 121-125).

Example 3

Association of Genes Encoding Human Cannabinoid CB1 and CB2 Receptors with Human Osteoporosis To investigate whether the causative role of cannabinoid receptor dysfunction in decreasing bone mass applies to the development of complex inherited human osteoporosis, a genetic association study using the case-control approach has been employed.

Materials aid Experimental Methods

Study subjects—Study subjects were post-menopausal osteoporotic patients (cases) and age-matched healthy individuals (controls) which were recruited in the Hôpital Lariboisière in Paris. Informed consent for genotyping of osteoporosis candidate genes was obtained from all participants following approval of the study by the Internal Review Board of the hospital.

Clinical assessment of cases—Bone mineral density (BMD) of the lumbar spine (L2-L4) or femoral (FN) neck was determined by dual energy x-ray absorptiometry (DEXA) using the same LUNAR DPX-L densitometer (Madison, Wis., USA) in all subjects. T-score values were based on a French population reference provided by the manufacturer. Exclusion criteria were medical history of malignancy, malabsorption, osteomalacia, hypogonadism, hemochromatosis, hyperthyroidism, hyperparathyroidism, renal insufficiency, endogenous or exogenous hypercortisolism and alcoholic cirrhosis. None of the subjects had plasma hormone abnormalities (TSH or parathyroid hormone). Women who had received treatment known to affect BMD for more than a month were also excluded.

Osteoporosis diagnosis—The diagnosis of osteoporosis was based on a T-score below −2.5 at L2-L4 or FN. The osteoporotic individuals were 63.1±9.4 years old (mean±SD); their body mass index (BMI) was 23±3 kg/m$^2$ (mean±SD). The control subjects had no previous femoral neck fracture or vertebral fractures detected on a routine X-ray of the lumbar spine. Their T-score was −2.5 or higher and their respective age and BMI were 63.4±6.3 years and 24.8±3.7 kg/m$^2$ (mean±SD).

Genomic DNA Analysis—Genomic DNA samples were extracted from peripheral leukocytes using standard protocols. Genomic DNA (20 ng) was amplified using the TaqMan Universal PCR Master Mix, No AmpErase® UNG, and Assays-On-Demand™ SNP Genotyping Products (all of which from Applied Biosystems, Foster City, Calif.). The SNP Genotyping Assay Mix contains sequence-specific forward and reverse primers to amplify the SNP of interest and two TaqMan® MGB probes. The probes detecting the specific sequence of each allele were labeled at their 5'-end to a reporter dye: VIC™ dye for allele 1 and FAM™ for allele 2, and at their 3'-end to a non-fluorescent quencher. PCR was performed through enzyme activation at 95° C. for 10 minutes followed by 40 cycles of the following steps: denaturation at 92° C. for 15 seconds, annealing and extension at 60° C. for 1 minute. As a result of the 5' nuclease activity of the polymerase, the probes were cleaved and hybridized to the target. Following PCR amplification, allelic discrimination was performed using an endpoint plate (ABI PRISM® 7700 Sequence Detection System, Applied Biosystems), which was analyzed using the SDS software (Applied Biosystems). The determination of both alleles was made manually based on the signals from each sample. Assays-On-Demand™ IDs (Applied Biosystems) used in this study are: C 79667, C 11546265, C 515477, C 515481, C 515482, C 310335, C 395615, C 1652594, C 1652590, C 1652585, C 1652583.

Table 3, hereinbelow, summarizes the list of all SNPs used and their genomic location.

TABLE 3

SNP IDs, sequences and genomic location

| Celera ID (NCB SNP reference number) | Gene Symbol (SNP type) | SEQ ID NO: | Context Sequence | Location on Celera Assembly |
|---|---|---|---|---|
| hCV79667 (rs4649119) | FUCA1; HMGCL (Intergenic/ Unknown) | SEQ ID NO:11 | AAGCTATAAGCAGTATAAGTTGAAA [C/G] TAGGAAAAGAAAGCTATACCATGTT | 22500418 |
| hCV11546265 | FUCA1; CNR2 (Intron) | SEQ ID NO:12 | TTGGGTATCCTTCATCTAACCAGAC [A/G] TGGCCATGAACTTCTGTAACGGTGT | 22520350 |
| hCV515477 (rs1130321) | CNR2; FUCA1 (3' UTR) | SEQ ID NO:13 | ACCTTAATCCTCATCATAGCATAGT [C/T] CTCGGTCCTCAGTGGCAAGGGTGAC | 22529155 |
| hCV515481 (rs4649124) | CNR2; FUCA1 (Silent Mutation) | SEQ ID NO:14 | AACCAACAGATGAGGAGCACAGCCA [A/G] CACTAGCCCTAGGGTCTTGGCCAAC | 22529988 |
| hCV515482 (rs2501431) | CNR2; FUCA1 (Silent Mutation) | SEQ ID NO:15 | CTAGTGCTGAGAGGACCCACATGAT [A/G] CCCAGGGTCACCAGTGCCCTTCCAC | 22530274 |
| hCV310335 (rs7530595) | CNR2; FLJ20312 (Intron) | SEQ ID NO:16 | GGTCTTACATGTAAATAGATGGCTC [C/T] GATATACCATTATTTTGGGGGGAGT | 22611809 |
| hCV395615 | CNR2; FLJ20312 (Intron) | SEQ ID NO:17 | CACCCAAAACTAACATAAAACACTA [C/T] GTAAAGATCCTCATCAAGTATCAGT | 22625334 |
| *rs2502992 | CNR2 (Missense Mutation) | SEQ ID NO:18 | (-) strand TCTATCTGATCCTGTCCTCCCACCG [A/G] CTCCGCCGGAAGGCCCTCATACCTGTTCATT | |
| rs2501432 | CNR2 (Missense Mutation) | SEQ ID NO:19 | GAACAGGTATGAGGGCTTCCGGCGGAGT [T/C] GGTGGGAGGACAGGATCAGATAGAGCACA | |
| hCV1652594 (rs806365) | CNR1 (Intergenic/ Unknown) | SEQ ID NO:20 | TCATAGCTAGCTCTTACTTTGTCTT [C/T] AGTGCTCTATTCAAGCATCACCTCT | 89263841 |
| hCV1652590 (rs1049353) | CNR1 (Silent Mutation) | SEQ ID NO:21 | ACATGGTTACCTTGGCAATCTTGAC [C/T] GTGCTCTTGATGCAGCTTTCTGCGG | 89271527 |
| hCV1652585 (rs806377) | CNR1 (Intron) | SEQ ID N0:22 | GCTTCTGAACCAGTTCTGCACACCT [C/T] TCCTGCAACTGTCATAGAATAAAGC | 89276615 |
| hCV1652583 (rs806380) | CNR1 (Intron) | SEQ ID N0:23 | TAACAGAGAACATACAAAGTTTTCA [A/G] TTAAGTAAAAGCCATGGCCATATTC | 89282545 |

Table 3: SNPs hCV79667, hCV11546265, hCV515477, hCV515481, hCV515482, hCV310335 and hCV395615 reside between the D1S2864 and D1S234 DNA markers on chromosomal region 1p36.1, and SNPs hCV1652594, hCV1652590, hCV1652585 and hCV1652583 reside between the D6S1609 and D6S462 DNA markers on chromosomal region 6q14.
*= SNP rs2502992 includes two adjacent polymorphic nucleotides, the context of the SNP is presented with the rare nucleotide (G) before the polymorphic A/G nucleotide. All sequences are on the (+) strand, except where otherwise noted.

Statistical Analysis

Test for association—Association of a specific SNP to a disease was evaluated in a case-control study by comparing the frequency of a specific allele and/or genotype in the case population (i.e., osteoporosis patients) with those of the control population using standard $\chi^2$ and proportion tests.

Odds ratios (OR)—is an estimate to the relative risk, i.e., the increased probability of disease in populations exposed to the risk allele OR together with approximate confidence intervals, were computed in a standard way using the Mantel-Haenszel estimator [Alan Agresti (1990). Categorical data analysis. New York: Wiley, pp. 59-66] in order to examine the magnitude (significance) and strength of the association between genotype and disease.

Genotype relative risk (GRR)—is the increased chance of an individual with a particular genotype to develop the disease. Thus, the GRR of the risk genotype G, with respect to the protective genotype $G_0$, is the ratio between the risk of an individual carrying genotype G to develop the disease, and the risk of an individual carrying genotype $G_0$ to develop the disease. The GRR used herein is represented in terms of an appropriate odds ratio (OR) of G versus $G_0$ in cases and controls. Computation of the GRR of the haplotypes was based on a multiplicative model in which the GRR of an homozygote individual was the square of the GRR of an heterozygote individual. For further details see Risch and Merikangas, 1996 [The future of genetic studies of complex human diseases. Science 273: 1516-1517].

Population attributable risk (PAR)—is the percentage of cases that would not have been affected if the population was monomorphic for the protective allele and genotype. The PAR value of a certain allele is calculated by the following equation: $(K-1)/K$, wherein K is $\Sigma \cdot f_i \cdot g_i$, $f_i$ is the frequency of the i genotype or double genotype and $g_i$ is the estimated GRR of the i genotype or double genotype, respectively.

COCAPHASE test—This method is based on likelihood ratio tests in a log-linear model; $\log(p/(1-p))=mu+sum\_i \{beta\_i \cdot x\_i\}$, wherein p is the probability of a chromosome being a "case" rather than a "control", x_i are variables that represent the haplotypes in some way depending upon the particular test, and mu and beta_i are coefficients to be estimated (Cordell & Clayton, 2002. AJHG 70:124).

Experimental Results

Low association between SNPs on the CNR1 locus and osteoporosis—The human central cannabinoid receptor gene (CNR1) (GenBank Accession No. U73304, SEQ ID NO:24) is located on the long arm of chromosome 6 (6q15). To test the hypothesis that a functional polymorphism in the cannabinoid receptor gene increases the risk for inherited osteoporosis, a case-control study was conducted using four single nucleotide polymorphisms (SNPs) covering a region of about 20 kb and encompassing the single coding exon of the CNR1 locus. As is shown in Table 4, hereinbelow, using the Taq-Man®-SNP assays the genotypic distributions of the two samples (i.e., case and control) did not deviate significantly ($p \geq 0.05$) from those expected from the Hardy-Weinberg equilibrium.

TABLE 4

Genotype frequencies of SNPs in the CNR1 locus in an osteoporosis case-control study

| SNP ID # | Genotypes controls | | | | Genotypes cases | | | |
|---|---|---|---|---|---|---|---|---|
| | 11 | 12 | 22 | Sum | 11 | 12 | 22 | Sum |
| hCV1652594 | 65 | 105 | 33 | 203 | 38 | 92 | 29 | 159 |
| hCV1652590 | 108 | 80 | 13 | 201 | 94 | 62 | 7 | 163 |
| hCV1652585 | 68 | 89 | 46 | 203 | 38 | 76 | 41 | 155 |
| hCV1652583 | 83 | 93 | 30 | 206 | 78 | 64 | 16 | 158 |

Table 4: Allele and genotype frequencies revealed by individual genotyping of SNPs in the CNR1 locus in an osteoporosis case-control study. "1" refers to the common allele of each SNP, i.e., C for SNP hCV1652594, C for hCV1652590, C for SNP hCV1652585 and A for SNP hCV1652583; "2" refers to the rare allele of each SNP, i.e., T for SNP hCV1652594, T for hCV1652590, T for SNP hCV1652585 and G for SNP hCV1652583.

Further analysis of the possible association between the four SNPs in the CNR1 locus with increased risk for osteoporosis revealed no significant differences of genotype or allele distributions of SNPs hCV1652594, hCV1652590, hCV1652585 between cases and controls. However, the distribution of the allele of SNP hCV 1652583 exhibited a P-value of 0.057 (Table 5, hereinbelow).

TABLE 5

Significance of association of SNPs in the CNR1 locus to osteoporosis

| | Allele 1 versus 2 | | | Genotype 11 versus 22 | | |
|---|---|---|---|---|---|---|
| SNP ID # | $\chi^2$ | P value | OR (95% C.I.) | $\chi^2$ | P value | OR (95% C.I.) |
| hCV1652594 | 1.84 | 0.17448 | 1.23 (0.91-1.65)[a] | 1.57 | 0.21065 | 1.50 (0.79-2.85)[a] |
| hCV1652590 | 0.90 | 0.34379 | 1.18 (0.84-1.65) | 0.98 | 0.32307 | 1.62 (0.62-4.22) |
| hCV1652585 | 2.88 | 0.08991 | 1.29 (0.96-1.74)[a] | 2.51 | 0.11287 | 1.60 (0.89-2.85)[a] |
| hCV1652583 | 3.63 | 0.05685 | 1.35 (0.99-1.85) | 2.69 | 0.10067 | 1.76 (0.89-3.48) |

Table 5: P values reflect the significance of differences between cases and controls as determined using the $\chi^2$ test.
OR = odd ratio.
C.I. = confidence interval.
[a] = For OR < 1, the inverted score is indicated.
"1" refers to the common allele of each SNP, i.e., C for SNP hCV1652594, C for hCV1652590, C for SNP hCV1652585 and A for SNP hCV1652583;
"2" refers to the rare allele of each SNP, i.e., T for SNP hCV1652594, T for hCV1652590, T for SNP hCV1652585 and G for SNP hCV1652583.

Altogether, these results demonstrate low association of SNPs in the CNR1 locus with the osteoporosis.

Significant association between SNPs in the CNR2 locus and osteoporosis—The human CNR2 gene (GenBank Accession No. NM_001841, SEQ ID NO:25) is located on the short arm of chromosome 1 (1p36), a region which has been implicated in the development of human osteoporosis by systematic genome-wide linkage studies (Devoto et al. 1998, Eur. J. Hum. Genet. 6: 151-7; Devoto et al., 2001, Human Molecular Genetics, 10: 2447-2452). The CNR2 gene consists of at least two exons, of which, the first is a non-coding exon, which is positioned approximately 37 Kb upstream of the second, coding exon. Genotyping of the hCV515477, hCV515481, and hCV515482 SNPs from exon 2 of CNR2 in 307 individuals, revealed a perfect correlation (data not shown), suggesting that these SNPs are in complete linkage disequilibrium. Thus, for further analysis the SNP hCV515481 (silent polymorphism) was used. As is shown in Table 6, hereinbelow, the genotypic distributions of the samples (i.e., case and control) did not differ from Hardy-Weinberg equilibrium ($p \geq 0.30$).

TABLE 6

Genotype frequencies of SNPs in the CNR2 locus in an osteoporosis case-control study

| | Genotypes controls | | | | Genotypes cases | | | |
|---|---|---|---|---|---|---|---|---|
| SNP ID # | 11 | 12 | 22 | Sum | 11 | 12 | 22 | Sum |
| hCV79667 | 49 | 92 | 59 | 200 | 60 | 81 | 18 | 159 |
| hCV11546265 | 87 | 80 | 34 | 201 | 78 | 65 | 15 | 158 |
| hCV515481[b] | 52 | 97 | 59 | 208 | 18 | 82 | 62 | 162 |
| hCV310335 | 60 | 104 | 36 | 200 | 63 | 73 | 20 | 156 |
| hCV395615 | 34 | 112 | 52 | 198 | 38 | 82 | 38 | 158 |

Table 6: Allele and genotype frequencies revealed by individual genotyping of SNPs in the CNR2 locus in an osteoporosis case-control study.

[b]= represents genotyping of SNPs hCV515477, hCV515482, rs2502992 and rs2501432 which were in complete linkage disequilibrium with hCV515481 and are therefore not shown. The distance between these three SNPs is: hCV515477 - 833 bp - hCV515481 - 286 bp - hCV515482.

"1" refers to the common allele of each SNP, i.e., C for SNP hCV79667, A for hCV11546265, A for SNP hCV515481, C for SNP hCV310335; and C for SNP hCV395615.

"2" refers to the rare allele of each SNP, i.e., G for SNP hCV79667, G for hCV11546265, G for SNP hCV515481, T for SNP hCV310335; and T for SNP hCV395615.

As is shown in Table 7, herein below, a significant difference was obtained in the allelic (p=0.00119) and genotypic (genotype 11 versus 22; p=0.00057) distributions of SNP hCV515481 (Table 7, hereinbelow). In addition, the odds ratios of the allele and genotype of SNP hCV515481 were 1.63 (95%, confidence interval: 1.21-2.20) and 3.04 (95% confidence interval: 1.60-5.78), respectively (Table 7, hereinbelow). These results strongly suggest an association of osteoporosis with SNP hCV515481.

TABLE 7

Significance of association of SNPs in the CNR2 gene to osteoporosis

| | Allele 1 versus 2 | | | Genotype 11 versus 22 | | |
|---|---|---|---|---|---|---|
| SNP ID # | $\chi^2$ | P value | OR (95% C.I.) | $\chi^2$ | P value | OR (95% C.I.) |
| hCV79667 | 17.62 | 0.00003 | 1.9 (1.41-2.57)[a] | 17.14 | 0.00004 | 4.01 (2.1-7.68)[a] |
| hCV11546265 | 3.60 | 0.05768 | 1.36 (0.99-1.86) | 4.27 | 0.03886 | 2.03 (1.03-4.01) |
| hCV515481[b] | 10.51 | 0.00119 | 1.63 (1.21-2.20)[a] | 11.87 | 0.00057 | 3.04 (1.60-5.78)[a] |
| hCV310335 | 4.40 | 0.03592 | 1.38 (1.02-1.88) | 3.72 | 0.05378 | 1.89 (0.83-2.70) |
| hCV395615 | 1.46 | 0.22751 | 1.20 (0.89-1.61) | 1.79 | 0.18096 | 1.53 (0.82-2.85) |

Table 7: P values reflect the significance of differences between cases and controls as determined using the $\chi^2$ test.

OR = odd ratio.

C.I. = confidence interval.

[a]= For OR < 1, the inverted score is indicated.

[b]= represents genotyping of SNPs hCV515477 and hCV515482 which were in complete linkage disequilibrium with hCV515481 and are therefore not shown. The distance between these three SNPs is: hCV515477 - 833 bp - hCV515481 - 286 bp - hCV515482.

"1" refers to the common allele of each SNP, i.e., C for SNP hCV79667, A for hCV11546265, A for SNP hCV515481, C for SNP hCV310335; and C for SNP hCV395615.

"2" refers to the rare allele of each SNP, i.e., G for SNP hCV79667, G for hCV11546265, G for SNP hCV515481, T for SNP hCV310335; and T for SNP hCV395615.

To further substantiate the involvement of the CNR2 locus in osteoporosis, three additional SNPs from the CNR2 locus (SNPs hCV11546265, hCV310335 and hCV395615) were employed in the case-control study: SNP hCV11546265 is located approximately 10 kb 3'-prime of the CNR2 gene, SNPs hCV310335 and hCV395615 are located 80 kb and 93 kb, respectively, from the 5'-prime of the CNR2 gene (FIG. 1). The polymorphism hCV11546265, is located in the second intron of the FUCA1 gene (GenBank Accession No. BC017338), which encodes alpha-L fucosidase. As is shown in Table 7, hereinabove, this SNP did not reach statistical significance in the test for allelic association. (p=0.05768), but exhibited weak significance (p=0.03886), when genotypes 11 versus 22 were compared between cases and controls. SNP hCV310335, which is located between the genes CNR2 and FLJ20312 (GenBank Accession No. AK000319), showed a weak allelic association (p=0.03592), but no genotypic association (Table 7, hereinabove). The even more centromeric SNP hCV395615, which is located in the last intron of the FUSIP1 gene (GenBank Accession No. BC010074), encoding an arginine/serine rich splicing factor, did not show allelic nor genotypic association (p>0.18, Table 7, hereinabove).

Further genotyping of SNIP hCV79667 (rs4649119) which is located at between the 3-hydroxymethyl-3-methyl-glutaryl-Coenzyme A lyase (hydroxymethylglutaricaciduria, HMGCL) and the fucosidase, alpha-L-1, tissue (FUCA1) revealed a highly significant difference of allelic (p=0.00003) and genotypic (genotype 11 versus 22; p=0.00002) distributions. In addition, the odds ratios for the allele and genotype of this SNP are 1.9 (95% confidence interval: 1.41-2.57) and 4.01 (95% confidence interval: 2.1-7.68), respectively (Table 7, hereinabove), suggesting a strong association of the risk allele and risk genotype, i.e., genotype 11 of hCV79667, with osteoporosis.

Significant association of the hCV79667-hCV11546265-hCV515481 haplotype with osteoporosis—The likelihood for the hCV79667-hCV11546265-hCV515481 (1-1-2) risk haplotype to associate with osteoporosis was calculated using the Cocaphase haplotype-analysis with sliding-window strategy. This analysis revealed a highly significant association of this specific haplotype with osteoporosis with a P value of $1.87 \times 10^{-27}$. Thus, carriers of the 1-1-2 haplotype of SNPs hCV79667-hCV11546265-hCV515481 have a highly increased risk to develop osteoporosis, whereas carriers of other specific haplotypes (1-2-2,1-2-1,2-1-2) have a highly significant reduced risk to develop osteoporosis. This is an enormously significant result for a complex disease, which strongly suggests a causative role of the CNR2 locus in human osteoporosis. Thus, it is very likely that polymorphisms, which are in linkage disequilibrium with the risk haplotype, cause osteoporosis.

The 1-1-2 hCV79667-hCV11546265-hCV515481 haplotype is more prevalent in osteoporosis cases—The 1-1-2 haplotype of the hCV79667-hCV11546265-hCV515481 SNPs was found to be present in 63% of the cases but in only 34% of the controls. These results suggest that the disease-causing SNP/SNPs is/are in linkage disequilibrium with the 1-1-2 hCV79667-hCV11546265-hCV515481 haplotype. On the other hand, the 1-2-2,1-2-1,2-1-2 hCV79667-hCV51546265-hCV515481 haplotypes were found in 3%, 10% and 16%, respectively, of the controls but never in the cases. These results are compatible with the existence of haplotypes, which carry protective polymorphism(s).

Altogether, these results demonstrate that SNPs of the 1-1-2 hCV79667-hCV11546265-hCV515481 risk haplotype and/or other SNPs which are in linkage disequilibrium with any of the SNPs in this haplotype, and/or with SNPs which are in linkage disequilibrium with the hCV515477 and hCV515482 SNPs call be used as diagnostic markers for osteoporosis.

The Glutamine to Arginine (63Q/R) missense mutation is associated with osteoporosis—The Gln/Arg non-synonymous polymorphism at position 63 of the CB2 protein (GenBank Accession No. NP_001832, SEQ ID NO:26) is encoded by the CAA→CGG nucleic acid change at positions 314 and 315 of the CB2 mRNA sequence (GenBank Accession No. NM_001841, SEQ ID NO:25) This amino acid change is represented by two SNPs: rs2502992 and rs2501432 (See Table 3, hereinabove). Sequencing of 344 individuals revealed that the CGG nucleic acid triplet coding the Arginine polymorph at position 63 of the CB2 protein is in tight linkage disequilibrium with the presence of the G allele of SNP hCV515481. Given the significant association of the G allele of SNP hCV515481 with osteoporosis (p=$1.2 \times 10^{-3}$), these results demonstrate that the presence of an Arginine residue at position 63 of the CB2 protein is associated with osteoporosis.

Thus, these results suggest the use of the Glutamine to Arginine missense mutation in determining predisposition of individuals to osteoporosis. In addition, the Gln/Arg missense mutation can be used to improve the diagnosis of osteoporosis in individuals suspected of having osteoporosis.

Moreover, these results suggest that other causative SNP(s) involving in osteoporosis are in linkage disequilibrium with at least one SNPs of the hCV79667-hCV11546265-hCV515481 risk haplotype.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank accession numbers mentioned in this specification are herein incorporated in their entirety by reference into the specification, to the same extent as if each individual publication, patent or patent application or GenBank accession number was specifically and individually indicated to be incorporated herein by reference. In addition, citation or identification of any reference in this application shall not be construed as an admission that such reference is available as prior art to the present invention.

What is claimed is:

1. A method of determining if a human individual is predisposed to osteoporosis, the method comprising: obtaining a nucleic acid sample from said human individual and analyzing said nucleic acid sample to determine the identity of a polymorphic variant at position 26 of SEQ ID NO: 14; wherein the presence of a guanine at position 26 of SEQ ID No: 14 is indicative of a predisposition to osteoporosis.

* * * * *

SEQUENCE LISTING

<160> NUMBER OF SEQ ID NOS: 26

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
tggtgtatga tgtctttggg                                               20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
atgctggctg tgttattggc                                               20

<210> SEQ ID NO 3
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 3
aacggtggct tggagttcaa c                                             21

<210> SEQ ID NO 4
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 4
taggtagcgg tcaacagcgg ttag                                          24

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
gacacaagca ttcccactat                                               20

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
atcagcagta accacagtca                                               20

<210> SEQ ID NO 7
<211> LENGTH: 21

<212> TYPE: DNA
<213> ORGANISM: Artificial sequence
<220> FEATURE:
<223> OTHER INFORMATION: Single strand DNA oligonucleotide

<400> SEQUENCE: 7
caagaagtgg atcatccagg t                                                      21

<210> SEQ ID NO 8
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 8
gctgctactc ccacttcgtg cttt                                                   24

<210> SEQ ID NO 9
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 9
gagaccttca acaccccagc c                                                      21

<210> SEQ ID NO 10
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 10
ggccatctct tgctcgaagt c                                                      21

<210> SEQ ID NO 11
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: SNP variation: C or G

<400> SEQUENCE: 11
aagctataag cagtataagt tgaaantagg aaaagaaagc tataccatgt t                     51

<210> SEQ ID NO 12
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: SNP variation: A or G

<400> SEQUENCE: 12
ttgggtatcc ttcatctaac cagacntggc catgaacttc tgtaacggtg t                     51

<210> SEQ ID NO 13
<211> LENGTH: 51
<212> TYPE: DNA
<213> ORGANISM: Homo sapiens
<220> FEATURE:

```
<221> NAME/KEY: misc_feature
<222> LOCATION: (26)..(26)
<223> OTHER INFORMATION: SNP variation: C or T

<400> SEQUENCE: 13
accttaatcc tcatcatagc atagtnctcg gtcctcagtg gcaagggtga c            51

<210> SEQ ID NO 14
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: SNP variation: A or G

<400> SEQUENCE: 14
aaccaacaga tgaggagcac agccancact agccctaggg tcttggccaa c            51

<210> SEQ ID NO 15
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: SNP variation: A or G

<400> SEQUENCE: 15
ctagtgctga gaggacccac atgatnccca gggtcaccag tgcccttcca c            51

<210> SEQ ID NO 16
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: SNP variation: C or T

<400> SEQUENCE: 16
ggtcttacat gtaaatagat ggctcngata taccattatt ttgggggag t             51

<210> SEQ ID NO 17
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: SNP variation: C or T

<400> SEQUENCE: 17
cacccaaaac taacataaaa cactangtaa agatcctcat caagtatcag t            51

<210> SEQ ID NO 18
<211> LENGTH: 56
<212> TYPE: DNA
<213> ORGANISM: Homo sapiens
<220> FEATURE:
<221> NAME/KEY: misc_feature
<222> LOCATION: (26)..(26)
<223> OTHER INFORMATION: SNP variation: A or G

<400> SEQUENCE: 18
tctatctgat cctgtcctcc caccgnctcc gccggaagcc ctcatacctg ttcatt       56
```

```
<210> SEQ ID NO 19
<211> LENGTH: 58
<212> TYPE: DNA
<213> ORGANISM: Homo sapiens
<220> FEATURE:
<221> NAME/KEY: misc_feature
<222> LOCATION: (29)..(29)
<223> OTHER INFORMATION: SNP variation: C or T

<400> SEQUENCE: 19
gaacaggtat gagggcttcc ggcggagtng gtgggaggac aggatcagat agagcaca      58

<210> SEQ ID NO 20
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: SNP variation: C or T

<400> SEQUENCE: 20
tcatagctag ctcttacttt gtcttnagtg ctctattcaa gcatcacctc t             51

<210> SEQ ID NO 21
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: SNP variation: C or T

<400> SEQUENCE: 21
acatggttac cttggcaatc ttgacngtgc tcttgatgca gctttctgcg g             51

<210> SEQ ID NO 22
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: SNP variation: C or T

<400> SEQUENCE: 22
gcttctgaac cagttctgca cacctntcct gcaactgtca tagaataaag c             51

<210> SEQ ID NO 23
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: SNP variation: A or G

<400> SEQUENCE: 23
taacagagaa catacaaagt tttcanttaa gtaaaagcca tggccatatt c             51

<210> SEQ ID NO 24
<211> LENGTH: 5665
<212> TYPE: DNA
<213> ORGANISM: Homo sapiens

<400> SEQUENCE: 24
tttgttttta ttcttcctgt ttctcaccat tcggcttatt tgttttccct cctcttagga    60
```

-continued

```
ttgcccctg tgggtcactt tctcagtcat tttgagctca gcctaatcaa agactgaggt      120
tatgaagtcg atcctagatg gccttgcaga taccaccttc cgcaccatca ccactgacct      180
cctgtacgtg ggctcaaatg acattcagta cgaagacatc aaaggtgaca tggcatccaa      240
attagggtac ttcccacaga aattcccttt aacttccttt aggggaagtc ccttccaaga      300
gaagatgact gcgggagaca accccagct agtcccagca gaccaggtga acattacaga      360
attttacaac aagtctctct cgtccttcaa ggagaatgag gagaacatcc agtgtgggga      420
gaacttcatg gacatagagt gtttcatggt cctgaacccc agccagcagc tggccattgc      480
agtcctgtcc ctcacgctgg gcaccttcac ggtcctggag aacctcctgg tgctgtgcgt      540
catcctccac tcccgcagcc tccgctgcag gccttcctac cacttcatcg gcagcctggc      600
ggtggcagac ctcctgggga gtgtcatttt tgtctacagc ttcattgact ccacgtgtt       660 ccaccgcaaa gatagccgca acgtgtttct gttcaaactg ggtggggtca cggcctcctt      720
cactgcctcc gtgggcagcc tgttcctcac agccatcgac aggtacatat ccattcacag      780 gccctggcc tataagagga ttgtcaccag gcccaaggcc gtggtagcgt tttgcctgat       840
gtggaccata gccattgtga tcgccgtgct gcctctcctg ggctggaact gcagaaaact      900
gcaatctgtt tgctcagaca ttttcccaca cattgatgaa acctacctga tgttctggat      960
cggggtcacc agcgtactgc ttctgttcat cgtgtatgcg tacatgtata ttctctggaa     1020
ggctcacagc cacgccgtcc gcatgattca gcgtggcacc cagaagagca tcatcatcca     1080
cacgtctgag gatgggaagg tacaggtgac ccggccagac caagcccgca tggacattag     1140
gttagccaag accctggtcc tgatcctggt ggtgttgatc atctgctggg cccctctgct     1200
tgcaatcatg gtgtatgatg tctttgggaa gatgaacaag ctcattaaga cggtgtttgc     1260
attctgcagt atgctctgcc tgctgaactc caccgtgaac cccatcatct atgctctgag     1320
gagtaaggac ctgcgacacg ctttccggag catgtttccc tcttgtgaag gcactgcgca     1380
gcctctggat aacagcatgg gggactcgga ctgcctgcac aaacacgcaa acaatgcagc     1440
cagtgttcac agggccgcag aaagctgcat caagagcacg gtcaagattg ccaaggtaac     1500
catgtctgtg tccacagaca cgtctgccga ggctctgtga gcctgatgcc tccctggcag     1560
cacaggaaaa gaatttttt ttttaagctc aaaatctaga agagtctatt gtctccttgg     1620 ttatatttt ttaactttac catgctcaat gaaaaggtga ttgtcaccat gatcacttat      1680
cagtttgcta atgtttccat agtttaggta ctcaaactcc attctccagg ggtttacagt     1740
gaagaaagcc tgttgtttaa gtgactgaac gatccttcaa agtctcaatg aaataggagg     1800 gaaaccttttg gctacacaat tggaagtcta agaacccatg gaaaaatgcc atcaaatgaa    1860
taatgccttt gtaaccacaa ctttcactat aatgtgaaat gtaactgtcc gtagtatcag     1920
agatgtccat ttttacaagt tatagtacta gagatatttt gtaaaatgta ttatgtcctg     1980
tgagatgtgt atcagtgttt atgtgctatt aatatttgtt tagttcagca aaactgaaag     2040 gtagacttt atgagaacaa tggacaagca gtggatacgt gtcaatgtgt gcactttttt      2100
tctatattat tgcccatgat ataactttag aaataaacct taatatttct tcaaatatct     2160
ctatttaatt ttgacactga ataaccgta aaggtttatt tttctgttac ctcaacaaga      2220
agaatttgaa gacttcaaaa tattgagcag aattcattca tacttaaaaa tttattagcc     2280
ctgcattttc ataggaagac acattatctt ctggactata gctgttctaa tggattataa     2340
tcagaatgga agagagaaag catattgact ttttttgagc gacatctctg actttctta      2400 gtctttagct attactggat ctcttaagac agcatgtgtt aatcttaatg tatatcgtta     2460
```

```
tcactgtgca gttgctgttt acttgaatag tattgtgttc ctatattcca ggtttaagta    2520
gatttcatgc ctgggtggcc aaacaacagt cttcattttt tttaattgaa agaagtagt    2580 gtctggatca gtaaaattat actgtgtgtg agtgtgaata taaatgtgtg tatgtgtgtt    2640
tctgtccgta actgttacag taatgtcata aagtgagaaa actgtgacca agtataaact    2700
tttaccactt gctgcactct tgcacatgga ttcagtttct aaaattgagt tcttcctgta    2760
atcttgttga taaaaatact gactccaacc attcaaaaat ttcaccccat ccctccttaa    2820
gagattggat caagtattac taaattgacc tttaggtatt acacaagacc agtgcttagc    2880
aaaaaataat gacaggcatc caaggaaggg atgtatttgt agtgttattg ccaggaaagg    2940
agagtacttt ggtttctgag caccgaatat tgagcaatat gtcagtcact aaaaggaaga    3000
cagttctaca gaaaaacaaa tggtaacatt tttcaatagc gtgtgtagat agtatgcact    3060
atatacatca cgttaaagta ggactatcac acccagccca tgtggctaaa aaagctgaat    3120
cagacagtgg atgagacaca caacggcagt gaagaaccga tacacttggc attgacgtct    3180
agctatgctg tatctgtgct ttgcccacat gcccttggtg acagctgagc acccagctct    3240
gtcttggtag gtttgggcta aggaacaaat ctctcctttg ctcgtggtta gcaagataca    3300
ctcaagcatg aagataaaca cagctgcttt cttcttacac cccggtctca tgctccttaa    3360
tggcgccatg ggtgcttgtt gggccttttt ccagtaagga atgatattgc tgaagaatct    3420
acttaaccct gacaaatttt aattataatc tcttcttata cagataaaac atgactccta    3480
caaggcccca aggtttacat agtctgaagt gaagtacaga gctggcatct atctggtgat    3540
ttctagctct cgagataccc aagcagcctg atggggcagt tccccttctt acggttcacg    3600
ctctaaggca ggatgtggct tatgagatac tttgcattgt ctgtctgcac accttgaatc    3660
tgcctgctgg ctcccttact ttacctctct gtcatgtgca gatgaaggct cagggtgcta    3720
gaggattagt aagatctctt tctaaagaca ggagagatta tttacaagaa gaactcacca    3780
gggtttagtt tgcatttaag aattgccagt ctttgtcct gcatcatctt gaacattaat    3840
ccacatgttt cagagctcac caggcagtac caatgctctt ttcacagcta tgaagagcta    3900
gagaaattct tgttatggta gaaaaatttc acggttcatt tttgaaactg catttgtgcg    3960
tatgcagtgt agattttata gtgtgttgtg ctttcaagat ctaaatcata tataataaat    4020
taagggacaa tggggctgac agcactaaac ttggtgctta ttgatattct aagaaatatc    4080
tgtgaaatat catcacgtat gttatacaac cttcatttaa aaaggtttaa aactagttag    4140
attcactttg acactttca tatcatttct taacccaagt gacgaaaaca ttgtccccaa    4200
tgaatatact cattagaatt accatttgtt aatatcactc attaattaac cccataatta    4260
gatccattaa tttaaatgat ttaaatttaa gtaagtttta taaggtctga catcagaggt    4320
atcttacttt cctctgagga tgatgtactt gccctgacca tgcattttac catcacacat    4380
gttcagaaag ggccaaattc ccaacctgct catttttttt tttatcagag tcatgatgaa    4440
tcagtcctag aatgtttcat ttgcacaagt agggctgcct ccaagaggaa cctctgattt    4500
attttgtatg aaatatatgt gaaaggatat gaatctgaga gatgctgtag acatctgtcc    4560
tacacttgag atgatttcca agcctctctg gcactttgag ttaagtctat ctggtattaa    4620
atgccaagga ccttttgctg cctaaatcca ctctgcagga aataggccca accaccagat    4680
gagaattagg ccctggatga gtagcgctat agttactgtc ctgttgatta atttctgcca    4740
tttcatgtcc ataaaagaga ccacccatat catgcacaca attagatttc tcacactcta    4800
```

-continued

```
actgtatatt tgtatgatat tttaaaatct cctaaatgct gggcaatggc tattaacaat    4860
taattgtctt gcactggcct tctgatgaaa tgttaacaat gcctattgta atatagaaaa    4920
aaacattcta tctactgatt tgggctgaat gtatgtaaat aggtttctaa aaagtcagat    4980
gtttgagcag tggcctacaa atcagtaatt ttcgggtggg agagtttctt tacattgccg    5040
tggcatctta aaagctatct tcatgtaaat tgactgtact aggcctactg gggatcagag    5100
ttcccaagaa aggaaacctt tcttgtatc tggattcaaa tttatttcca atgtttcaag    5160
cgggaaacat gactctttat tgtctgtaaa tctaacatta ttacttttcc tcttagaaga    5220
atattgtatt gttagatgtt tgttgagctg gtaacatcgt tgcaaccact gcaatatctt    5280
cgttagtaat ctgtataata ctttgtatac aagtactggt aagattgtta ttaaatgtag    5340
cttcagtcat taaattacta tagcaaagta gtacttcttc tgtaatattt acaatgtatt    5400
aagcccacag tatattttat ttcaatgtaa ttaaactgtt aacttattca aagagaaaac    5460
atctcatcat gtctattgtc caaagttacc tggaatcaaa taaaaattct agattaccat    5520
gaagaacata aaatgccttt gaactctgcc ttatttcaca gtctgatggc aaaatactaa    5580
ggatttaatt tctaaaagat tgctgaacta atttattcct caaaaagcac taatgactac    5640
ttgaaaagtg gggacatatt ggatt                                          5665
```

```
<210> SEQ ID NO 25
<211> LENGTH: 1776
<212> TYPE: DNA
<213> ORGANISM: Homo sapiens
<220> FEATURE:
<221> NAME/KEY: misc_feature
<222> LOCATION: (314)..(315)
<223> OTHER INFORMATION: Non-synonymous polymorphism: AA or GG

<400> SEQUENCE: 25
```

```
caggtcctgg gagaggacag aaaacaactg gactcctcag cccccggcag ctcccagtgc      60
ccagccaccc acaacacaac ccaaagcctt ctagacaagc tcagtggaat ctgaagggcc     120
caccccatgg aggaatgctg ggtgacagag atagccaatg gctccaagga tggcttggat     180
tccaacccta tgaaggatta catgatcctg agtggtcccc agaagacagc tgttgctgtg     240
ttgtgcactc ttctgggcct gctaagtgcc ctggagaacg tggctgtgct ctatctgatc     300
ctgtcctccc accnnctccg ccggaagccc tcatacctgt tcattggcag cttggctggg     360
gctgacttcc tggccagtgt ggtctttgca tgcagctttg tgaatttcca tgttttccat     420
ggtgtggatt ccaaggctgt cttcctgctg aagattggca gcgtgactat gacctttcaca    480 gcctctgtgg gtagcctcct gctgaccgcc attgaccgat acctctgcct gcgctatcca     540
ccttcctaca agctctgctc cacccgtgga agggcactgg tgaccctggg catcatgtgg     600
gtcctctcag cactagtctc ctacctgccc ctcatgggat ggactgctg tcccaggccc     660 tgctctgagc ttttcccact gatccccaat gactacctgc tgagctggct cctgttcatc     720
gccttcctct tttccggaat catctacacc tatgggcatg ttctctggaa ggcccatcag     780
catgtggcca gcttgtctgg ccaccaggac aggcaggtgc aggaatggcc gaatgagg      840 ctggatgtga ggttggccaa gaccctaggg ctagtgttgg ctgtgctcct catctgttgg     900
ttcccagtgc tggccctcat ggcccacagc ctggccacta cgctcagtga ccaggtcaag     960 aaggccttg ctttctgctc catgctgtgc ctcatcaact ccatggtcaa ccctgtcatc    1020
tatgctctac ggagtggaga gatccgctcc tctgcccatc actgcctggc tcactggaag    1080
aagtgtgtga ggggccttgg gtcagaggca aaagaagaag ccccgagatc ctcagtcacc    1140
```

-continued

```
gagacagagg ctgatgggaa aatcactccg tggccagatt ccagagatct agacctctct    1200
gattgctgat gaggcctctt cccaatttaa acaactcaag tcagaaatca gttcactccc    1260
tggaagagag agagggtct  tggcactctc ttcttactta aaccagtccc agacacctag    1320
acacggaccc cttttgctg  atgagtgttg ggactgactc ctggaagaca gcctggcctt    1380
gcccacctgc acacagtctg ttggataggt agggccacga ggagtagcca ggtaggcgag    1440
acacaaaaag gcctgggaca gggtcagtac aagtcaggac aggcttcatg cctgcatcct    1500
ccagagacca ccaggagcca aagcgagcct ccaggcccag caatgaggga cttgggagaa    1560
atctgagaag aatgggttgt tctcttggga agtcagggta tcagatggga tggacatcca    1620
ggtcttctct ctgcctaatt gtcaaggcct ccttggctct ggagctatga aaggccccac    1680
tttcaagtca cccttgccac tgaggaccga ggactatgct atgatgagga ttaaggtgtt    1740
gacttgcctc tttcagagat aaatgacaag ccttca                              1776
```

```
<210> SEQ ID NO 26
<211> LENGTH: 360
<212> TYPE: PRT
<213> ORGANISM: Homo sapiens
<220> FEATURE:
<221> NAME/KEY: misc_feature
<222> LOCATION: (63)..(63)
<223> OTHER INFORMATION: Non-synonymous polymorphism: Gln or Arg

<400> SEQUENCE: 26

Met Glu Glu Cys Trp Val Thr Glu Ile Ala Asn Gly Ser Lys Asp Gly
1               5                   10                  15

Leu Asp Ser Asn Pro Met Lys Asp Tyr Met Ile Leu Ser Gly Pro Gln
                20                  25                  30

Lys Thr Ala Val Ala Val Leu Cys Thr Leu Gly Leu Leu Ser Ala
            35                  40                  45

Leu Glu Asn Val Ala Val Leu Tyr Leu Ile Leu Ser Ser His Xaa Leu
        50                  55                  60

Arg Arg Lys Pro Ser Tyr Leu Phe Ile Gly Ser Leu Ala Gly Ala Asp
65                  70                  75                  80

Phe Leu Ala Ser Val Val Phe Ala Cys Ser Phe Val Asn Phe His Val
                85                  90                  95

Phe His Gly Val Asp Ser Lys Ala Val Phe Leu Leu Lys Ile Gly Ser
            100                 105                 110

Val Thr Met Thr Phe Thr Ala Ser Val Gly Ser Leu Leu Leu Thr Ala
        115                 120                 125

Ile Asp Arg Tyr Leu Cys Leu Arg Tyr Pro Pro Ser Tyr Lys Ala Leu
    130                 135                 140

Leu Thr Arg Gly Arg Ala Leu Val Thr Leu Gly Ile Met Trp Val Leu
145                 150                 155                 160

Ser Ala Leu Val Ser Tyr Leu Pro Leu Met Gly Trp Thr Cys Cys Pro
                165                 170                 175

Arg Pro Cys Ser Glu Leu Phe Pro Leu Ile Pro Asn Asp Tyr Leu Leu
            180                 185                 190

Ser Trp Leu Leu Phe Ile Ala Phe Leu Phe Ser Gly Ile Ile Tyr Thr
        195                 200                 205

Tyr Gly His Val Leu Trp Lys Ala His Gln His Val Ala Ser Leu Ser
    210                 215                 220

Gly His Gln Asp Arg Gln Val Pro Gly Met Ala Arg Met Arg Leu Asp
225                 230                 235                 240
```

-continued

```
Val Arg Leu Ala Lys Thr Leu Gly Leu Val Leu Ala Val Leu Leu Ile
            245                 250                 255

Cys Trp Phe Pro Val Leu Ala Leu Met Ala His Ser Leu Ala Thr Thr
            260                 265                 270

Leu Ser Asp Gln Val Lys Lys Ala Phe Ala Phe Cys Ser Met Leu Cys
            275                 280                 285

Leu Ile Asn Ser Met Val Asn Pro Val Ile Tyr Ala Leu Arg Ser Gly
            290                 295                 300

Glu Ile Arg Ser Ser Ala His His Cys Leu Ala His Trp Lys Lys Cys
305                 310                 315                 320

Val Arg Gly Leu Gly Ser Glu Ala Lys Glu Glu Ala Pro Arg Ser Ser
                325                 330                 335

Val Thr Glu Thr Glu Ala Asp Gly Lys Ile Thr Pro Trp Pro Asp Ser
            340                 345                 350

Arg Asp Leu Asp Leu Ser Asp Cys
            355                 360
```